(12) United States Patent
Roy

(10) Patent No.: US 9,364,568 B2
(45) Date of Patent: Jun. 14, 2016

(54) METHODS TO DIAGNOSE DEGENERATIVE DISC DISEASE

(75) Inventor: Josee Roy, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 510 days.

(21) Appl. No.: 12/836,609

(22) Filed: Jul. 15, 2010

(65) Prior Publication Data

US 2012/0014868 A1   Jan. 19, 2012

(51) Int. Cl.
*A61K 49/00* (2006.01)
*A61B 6/00* (2006.01)

(52) U.S. Cl.
CPC .............. *A61K 49/0054* (2013.01); *A61B 6/506* (2013.01)

(58) Field of Classification Search
None
See application file for complete search history.

(56) References Cited

U.S. PATENT DOCUMENTS

| | | |
|---|---|---|
| 6,229,024 B1 | 5/2001 | Schmued |
| 2002/0095144 A1 | 7/2002 | Carl |
| 2004/0010251 A1 | 1/2004 | Pitaru et al. |
| 2004/0220296 A1 | 11/2004 | Lowman et al. |
| 2006/0193768 A1 | 8/2006 | Cuthbertson |
| 2007/0190149 A1 | 8/2007 | Zahos |
| 2007/0196375 A1 * | 8/2007 | Tobinick ................ 424/145.1 |
| 2007/0202048 A1 | 8/2007 | Zanella et al. |
| 2007/0287991 A1 | 12/2007 | McKay et al. |
| 2007/0298407 A1 | 12/2007 | McKay et al. |
| 2008/0008988 A1 | 1/2008 | McKay et al. |
| 2009/0030308 A1 | 1/2009 | Bradford et al. |
| 2009/0076481 A1 | 3/2009 | Stegmann et al. |
| 2009/0130019 A1 | 5/2009 | Tobinick |
| 2009/0143863 A1 | 6/2009 | Perez-Cruet |
| 2009/0162351 A1 | 6/2009 | Brown et al. |

FOREIGN PATENT DOCUMENTS

WO   2007057908 A2   5/2007
WO   2007136673 A2   11/2007

OTHER PUBLICATIONS

Narula et al. Gamma imaging of atherosclerotic lesions: the role of antibody affinity in in vivo target localization. 1996 J. Nucl. Cardiol. 3: 231-241.*
Fujita et al. Vascular endothelial growth factor-A is a survival factor for nucleus pulposus cells in the intervertebral disc. 2008 Biochem. Biophys. Res. Commun. 372: 367-372.*
Lee et al. Comparison of growth factor and cytokine expression in patients with degenerated disc disease and herniated nucleus pulposus. 2009 Clin. Biochem. 42: 1504-1511. Published online Jun. 27, 2009.*
Ferrara et al. Discovery and development of bevacizumab, an anti-VEGF antibody for treating cancer. 2004 Nat. Rev. Drug Discov. 3: 391-400.*

* cited by examiner

*Primary Examiner* — Michael G Hartley
*Assistant Examiner* — Jennifer Lamberski
(74) *Attorney, Agent, or Firm* — Sorell Lenna & Schmidt LLP

(57) ABSTRACT

Methods are provided that better describe, and localize the pain generator or suspected pain generator in and around spinal discs in relation to neck or back pain so as to improve the diagnosis of degenerative disc disease. In some embodiments, there are methods for diagnosing a pain generator or a suspected pain generator in a patient suffering from back pain, the methods comprise labeling an inflammatory, vascular, neuronal, and/or metabolic pain marker at a location inside of or adjacent to an intervertebral disc in the patient suffering from back pain to increase an image of the pain marker with an imaging procedure; and imaging the labeled inflammatory, vascular, neuronal, and/or metabolic pain marker in a manner sufficient to diagnose the pain generator or suspected pain generator.

8 Claims, 6 Drawing Sheets

METHODS TO DIAGNOSE DEGENERATIVE DISC DISEASE

BACKGROUND

The human spine is formed from twenty-six consecutive vertebrae. Each of these vertebrae is separated from any adjacent vertebra by an intervertebral disc that functions to absorb shock and prevent each vertebra from directly impacting upon another vertebra. At the center of each disc is a nucleus pulposus that contains proteoglycan. Around the nucleus pulposus is an outer ring called the annulus fibrosus. Degenerative disc disease refers to any of the common degenerative conditions of the spine involving degeneration of the disc. Disc degeneration is often associated with the symptom of pain and may lead to inflammation and neuropathic pain, for example, spinal stenosis, spondylolisthesis, and retrolisthesis.

Disc degeneration associated with the aging process is generally associated with the loss of proteoglycan from the nucleus pulposus of the spinal discs and a reduction of the disc's ability to absorb shock between vertebrae. Although some affected patients may not exhibit symptoms, many affected patients suffer from chronic back or neck pain in addition to arm and/or leg pain. Pain associated with disc degeneration may become debilitating and may greatly reduce a patient's quality of life.

Treatments for intervertebral disc herniations include open or mini-open surgery, using very small opening incisions or percutaneously, utilizing specially designed instruments and radiographic techniques to target the pain generator or area that is involved in the painful condition.

Unfortunately, particularly with pain generators in the spine, the cause for the back or neck pain may be difficult to diagnose, as there are numerous structures containing nociceptors and often the pain radiates throughout the back or neck region. To complicate matters for the practitioner, the vertebrae of the spine look very similar and are often no more than an inch tall with only a small separation between their bony structures. Sometimes, particularly when the spine is injured or abnormal, it may be difficult to locate the injured or abnormal vertebrae involved in causing the pain. Often times the practitioner will take additional steps such as taking several X-rays, MRIs, CAT scans, and counting the number of vertebrae to ensure the right vertebra is being treated. MRI and CT myelograms can detect anatomical changes associated with degeneration of the disc but they have no predictive value since it is well known that a really abnormal looking disc may not be painful and a minimally disrupted disc may be associated with severe pain. Alternative tests are based on injection of pain-provoking or local anesthetic fluid into the disc (i.e. discography) while the patient is asked if the procedure "reproduces exactly" or "annihilates completely" his/her original pain symptoms. These tests are of a very invasive and subjective nature and their predictive value remains controversial. In addition, the discography procedure can actually trigger disc herniation at the site of injection.

The practitioner, sometimes, will let the disease degeneration and pain progress to a later stage to get a better understanding of the pain generator before starting treatment. Over time, the pain often radiates outside the back or neck region, for example into the arm or leg which is often caused by severe bulging of the disc that causes a pressure on the adjacent nerve root. The path of the radiating pain symptoms gives a better indication of which nerve root and spinal level is affected. Unfortunately, at this advanced stage of degeneration, the non-surgical treatment options are limited.

In spite of these additional steps, sometimes the wrong vertebra is indeed treated, which subjects the patient to additional surgeries. The patient will often feel afraid or depressed and this may prevent full participation in general rehabilitation programs and may even slow recovery. Thus, there is a need to improve the diagnosis of degenerative disc disease to increase the success rate of the currently available treatments and allow for the development of early and less invasive interventions. There is also a need to reduce surgical errors from practitioners operating on the wrong intervertebral disc.

SUMMARY

Methods are provided that better describe, and localize the pain generator or suspected pain generator in and around spinal discs in relation to back and neck pain so as to improve the diagnosis of degenerative disc disease. The methods provided utilize labels in the cancer imaging area to better diagnose degenerative disc disease.

In some embodiments, methods are provided that artificially label substances locally in the area of back or neck pain that are suspected pain generators. These areas include suspected pain generators at or near the disc, facet joints, and/or vertebral bodies.

In some embodiments, by the methods provided, the practitioner can rule out referred pain that is where the pain sensation is localized to an area completely unrelated to the site of injury. In some embodiments, the methods provided can dictate the location of the surgery and reduce the risk that the practitioner operates on the wrong area of the patient.

In some embodiments, by the methods provided, the practitioner can determine the progression of the disease and evaluate how effective is a treatment based on the presence, intensity and location of the pain marker within the affected tissue.

In one embodiment, there is a method for diagnosing a pain generator or a suspected pain generator in a patient suffering from back or neck pain, the method comprising labeling an inflammatory, vascular, neuronal, and/or metabolic pain marker at a location inside of or adjacent to an intervertebral disc in the patient suffering from back pain to increase an image of the pain marker with an imaging procedure; and imaging the labeled inflammatory, vascular, neuronal, and/or metabolic pain marker in a manner sufficient to diagnose the pain generator or suspected pain generator.

In another embodiment, there is a method for diagnosing a pain generator or a suspected pain generator in a patient suffering from degenerative disc disease, the method comprising determining an amount of labeled inflammatory, vascular, neuronal, and/or metabolic pain marker in a location inside of or adjacent to an intervertebral disc in the patient suffering from degenerative disc disease; and comparing the amount of labeled inflammatory, vascular, neuronal, and/or metabolic pain marker in a location inside of or adjacent to an intervertebral disc to a normal range of the labeled pain marker inside of or adjacent to an intervertebral disc, wherein the amount of the labeled pain marker outside of the normal range indicates the location of the pain generator or suspected pain generator.

In yet another embodiment, there is a method for diagnosing a pain generator or a suspected pain generator in a patient suffering from back pain, the method comprising administering a diagnostic agent to label an inflammatory, vascular, neuronal, and/or metabolic pain marker at a location inside of or adjacent to an intervertebral disc in the patient suffering from back pain to increase an image of the pain marker with an imaging procedure; and imaging the labeled inflammatory, vascular, neuronal, and/or metabolic pain marker in a manner sufficient to diagnose the pain generator or suspected pain generator.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

FIG. 3 illustrates an embodiment of the annulus fibrosus of a degenerating disc in which a labeled agent is released near neuronal and vascular extension pain generators, which will bind the neuronal and vascular pain markers and allow visualization of the neuronal and vascular extensions to locate the pain generators or suspected pain generators. The labeled agent can be administered, for example, intravenously, intramuscularly, subcutaneously or the like.

Figure 1:
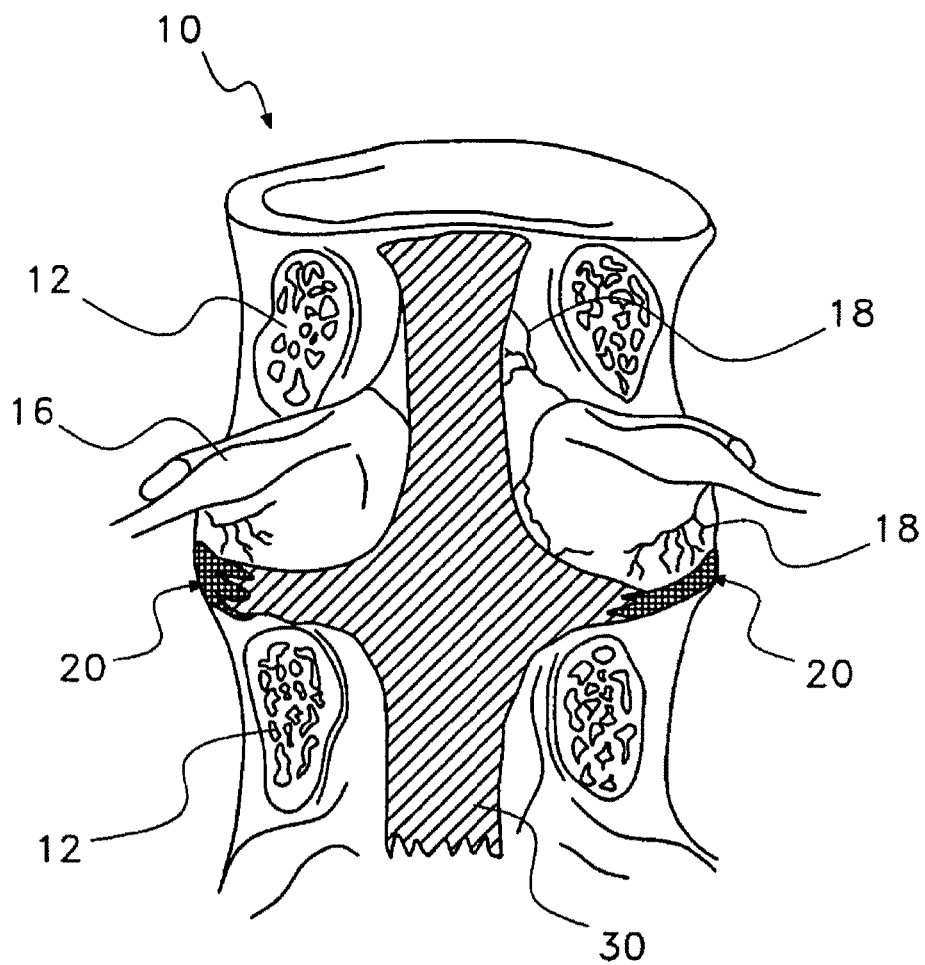
FIG. 1 illustrates a posterior perspective view of a spine.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

DEFINITIONS

It is noted that, as used in this specification and the appended claims, the singular forms "a," "an," and "the," include plural referents unless expressly and unequivocally limited to one referent. Thus, for example, reference to "a pain generator" includes one, two, three or more pain generators.

The term "diagnostic" or "diagnosing" means identifying the presence, absence, and/or location of one or more pain generators or suspected pain generators or disease state of the pain generators associated with the pain.

The term "diagnostic agent" is any moiety that may be used for diagnosis of a pain marker and/or a pain generator. For example, diagnostic agents include imaging agents containing radioisotopes such as indium or technetium; contrasting agents containing iodine, technetium, or gadolinium; enzymes such as horse radish peroxidase, GFP, alkaline phosphatase, or beta-galactosidase; fluorescent substances such as europium derivatives; luminescent substances such as N-methylacrydium derivatives or the like. Another example of a diagnostic agent is radionuclides, which may be detected using positron mission tomography (PET) or single photon emission computed tomography (SPECT) imaging or other methods known to one of skill in the art. In one embodiment, the diagnostic agent comprises one or more radionuclides labels: $^{131}I$, $^{125}I$, $^{123}I$, $^{99m}Tc$, $^{18}F$, $^{68}Ga$, $^{67}Ga$, $^{72}As$, $^{89}Zr$, $^{64}Cu$, $^{62}Cu$, $^{111}In$, $^{203}Pb$, $^{198}Hg$, $^{11}C$, $^{97}Ru$, and $^{201}Tl$ or a paramagnetic contrast agent, such as gadolinium, cobalt, nickel, manganese or iron. Such moieties may be chelated to their own metal binding domain which in turn could be coordinated to the metal ion found in the bridge to the hydrophobic group or hydrophilic group.

The term "at or near" is intended to include a region extending up to and including from 0 cm to 5 cm from the target tissue site (e.g., nerve, muscle, ligament, bone, vertebra, etc.), as well as interior regions within the target tissue site.

The term "pain" includes nociception and the sensation of pain, both of which can be assessed objectively and subjectively, using pain scores and other methods well-known in the art. Exemplary types of pain diagnosable by the methods and compositions of the present application include, without limitation, back pain in the lumbar regions (low back pain) or cervical region (neck pain), leg pain, sciatic pain, radicular pain (experienced in the lower back and leg from lumber pathology, or in the neck and arm from cervical pathology), or neuropathic pain of the arm, neck, back, lower back, leg, or related pain distributions resulting from disc or spine pathology. In some embodiments, the pain can be superficial somatic pain (or cutaneous pain), deep somatic pain that originates from ligaments, tendons, bones, blood vessels, fasciae, and/or muscles, visceral pain, and/or neuropathic pain or the like. As used herein, "neuropathic pain" includes pain arising from injury to the nerve root, dorsal root ganglion or peripheral nerve.

The term "pain generator" refers to the source or cause involved in the painful condition. The term "suspected pain generator" includes the source or cause believed to be involved in the painful condition, yet no definitive diagnosis of the location of the pain generator has been made. Pain generators can occur from, for example, vertebral abnormalities, such as, compression fractures, pars defects, vertebral instability, soft tissue abnormalities in ligaments, tendons, muscles, cartilaginous structures, joints (e.g., facet joints, intervertebral discs, sacroiliac joints, etc.) or abnormalities resulting from tumors, infection or other infiltrative processes. Pain generators can result from nerve root lesions (e.g., compressive lesions from adjacent discs, hypertrophic facet joints, facet joints cysts, faulty hardware positioning, bony foraminal encroachment, spondylolisthesis, spondylolysis, congenitally short pedicles, nerve sheath tumors, granulation tissue and/or arachnoiditis, etc.), spinal nerve compression (e.g., spinal stenosis), peripheral nerve lesions, femoral neuropathy, meralgia paresthetica, peroneal neuropathy, asymmetrical neuropathies, lower limb joint pathology, vascular pathology, degenerative disc and joint disease or the like. In some embodiments, the methods provided can be used to locate the pain generator that causes degenerative disc disease.

The term "pain marker" includes materials whether structural, chemical, or otherwise, that have an association, either directly or indirectly, with the pain generator such that by binding the pain generator, it provides a vehicle to enhance diagnosis or therapy in relation to the associated pain. In one particular example, pain markers relate to transmitting pain signals along or between nerves. In another embodiment, pain markers can stimulate pain, such as, for example, cytokines, growth factors, etc. Pain markers also include materials related to other points in a chemical or biological cascade related to pain, such as pain markers that relate to secondary or tertiary products or components of such pain generation or transmission process. If a marker is distinctly present (or absent) in a somewhat recognizable manner when and where pain is present, and in a different level or manner than when and where pain is not present, then it is considered a "pain marker" as herein described. This use of the term "marker" similarly applies in other contexts herein provided, such as for example "inflammatory markers", "metabolic markers,", "neuronal markers", "vascular markers," etc.

The term "label" includes a moiety that allows detection using imaging techniques. Labels include molecules capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., antibodies, antigen, antibody epitope, etc.), intercalating dyes or the like. Some examples of labels include, without limitation, $^{131}$I, $^{125}$I, $^{123}$I, $^{99}$mTc, $^{18}$F, $^{68}$Ga, $^{67}$Ga, $^{72}$As, $^{89}$Zr, $^{64}$Cu, $^{62}$Cu, $^{111}$In, $^{203}$Pb, $^{198}$Hg, $^{11}$C, $^{97}$Ru, and $2^{01}$Tl or a paramagnetic contrast agent, such as gadolinium, cobalt, nickel, manganese or iron.

It will be understood that the labeled marking of the pain marker or pain generator as herein described is of particular benefit with respect to the resulting image. While imaging the "labeled pain marker" or "labeled pain generator" may be generally described, it is to be understood that what is imaged by the particular imaging modality may include without limitation: the overall conjugate or combination of label-plus-pain marker; the label itself; the pain marker itself (e.g. to the extent modified in a recognizable way by the labeled marking), the pain generator itself (e.g. to the extent modified in a recognizable way by the label, or labeled pain marker); or combinations of the above.

The term "spinal surgery" includes a procedure in which one or more incisions are made and requires manipulation of spinal tissues, with or without removal and/or repair of spinal tissues. Examples of spinal surgery include, but are not limited to, repair of a herniated disc, adhesioloysis, radiofrequency neurotomy; intradiskal electrothermal therapy, fusion of vertebrae, full or partial discectomy, laminectomy, laminotomy, or laminoplasty, or the like.

The term "practitioner" means a person who is using the methods and/or devices of the current disclosure on the patient. This term includes, without limitation, doctors (e.g., surgeons, interventional specialists, physicians, etc.), nurses, nurse practitioners, other medical personnel, clinicians, veterinarians, or scientists.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

"Localized" delivery includes delivery where one or more diagnostic agents are deposited within a tissue, for example, a nerve root of the nervous system or a region of the brain, or in close proximity (within about 5 cm, or preferably within about 2 cm, or within about 1 cm, or less for example) thereto. A "targeted delivery system" provides delivery of one or more diagnostic agents at or near the target site as needed for treatment of pain, inflammation or other disease or condition.

Methods are provided that better describe, and localize the pain generator or suspected pain generator in and around spinal discs in relation to back pain so as to improve the diagnosis of degenerative disc disease. In some embodiments, methods are provided that artificially label substances locally in the area of back pain that are suspected pain generators. These areas include suspected pain generators at or near the disc, facet joints, and/or vertebral bodies.

In some embodiments, by the methods provided, the practitioner can rule out referred pain that is where the pain sensation is localized to an area completely unrelated to the site of injury. In some embodiments, the methods provided can dictate the location of the surgery and reduce the risk that the practitioner operates on the wrong area of the patient.

In one embodiment, there is a method for diagnosing a pain generator or a suspected pain generator in a patient suffering from back pain, the method comprising labeling an inflammatory, vascular, neuronal, and/or metabolic pain marker at a location inside of or adjacent to an intervertebral disc in the patient suffering from back pain to increase an image of the pain marker with an imaging procedure; and imaging the labeled inflammatory, vascular, neuronal, and/or metabolic pain marker in a manner sufficient to diagnose the pain generator or suspected pain generator.

In one embodiment, there is a method to evaluate the progression of the disease and how effective is a treatment comprising labeling an inflammatory, vascular, neuronal, and/or metabolic pain marker at a location inside of or adjacent to an intervertebral disc in the patient suffering from back pain and using image processing to determine the progression of the invading cells or cellular extensions within the deeper layers of the pain generator.

Back Pain

Back pain is a very difficult pain for practitioners throughout the world to treat. The reason often is inadequate diagnosis, or failure to identify the true pain generator. Methods are provided that better describe, and localize the pain generator or suspected pain generator in and around spinal discs in relation to back pain so as to improve the diagnosis of degenerative disc disease. By labeling an inflammatory, vascular, neuronal, and/or metabolic pain marker at a location inside of or adjacent to an intervertebral disc in the patient suffering from back pain, an enhanced image of the pain generator, if any, or suspected pain generator can be achieved and proper diagnosis of the location of the pain generator can be made. Thus the practitioner can identify the pain generator causing the back pain.

For example, lumbar spine pain falls into two general categories: purely axial, and radicular or radiating. In patients with purely midline or lateralizing low-back pain, common and uncommon etiologies should be considered. These include pain originating from osseous structures (vertebral compression fractures, pars defects, or vertebral instability), soft tissue (ligaments, tendons, muscles and cartilaginous structures), joints (facet joints, intervertebral discs, sacroiliac joints) as well as tumors, infection or other infiltrative processes. In patients with radicular pain, nerve root lesions (compressive lesions from adjacent discs, hypertrophic facet joints, facet joints cysts, faulty hardware positioning, bony foraminal encroachment caused by spondylolisthesis or spondylolysis, congenitally short pedicles, nerve sheath tumors, granulation tissue and arachnoiditis), spinal nerve compression and peripheral nerve lesions should be considered. In some embodiments, by labeling an inflammatory, vascular, neuronal, and/or metabolic pain marker, one can confirm diagnosis that the pain generator does not originate from the spine but is often misdiagnosed (often as classified as referred pain) such as, for example, femoral neuropathy, meralgia paresthetica, peroneal neuropathy, asymmetrical neuropathies, lower limb joint pathology or vascular pathology. These conditions are often mistaken for radicular pain in patients with and without radiographic evidence of degenerative disc and joint disease. Using the diagnostic methods of the present application, these conditions now can be more definitively diagnosed.

Spinal stenosis is another condition where the patient will exhibit, among other things, back pain. Spinal stenosis, either acquired or congenital, results from degenerative changes in the spine, variably including the intervertebral disks, the intervertebral joints (facet joints) and the ligamentum flavum. In each case, the degenerative changes together result in a gradual narrowing of the lumbar or cervical spinal canal, causing compression of the spinal cord and spinal nerve roots. Symptoms include: pain and/or numbness in the neck, back, buttocks, legs, thighs or calves that is worse with walking, standing and/or exercise; back pain that radiates to the legs; weakness of the legs; and difficulty or imbalance when walking. Patients can be diagnosed with spinal stenosis through, for example, persistent radiating pain; neurologic examination findings of abnormal sensation and muscle weakness in the legs; gait disturbances and characteristic bent over posture; asymmetric deep tendon reflexes; and radiologic findings of spinal stenosis by x-ray (e.g., myelogram), MRI, spinal CT or CT myelography or the like. Depending on whether the stenosis is central or foraminal, provocative maneuvers on physical examination such as side bending reproducing the pain may be negative or positive, respectively. In some embodiments, the better diagnostic imaging methods of the present application may be used to diagnose spinal stenosis.

Degenerative Disc Disease

Degenerative disc disease refers to any of the common degenerative conditions of the spine involving degeneration of the disc. Disc degeneration is often associated with the symptoms of back pain and may lead to inflammation and neuropathic pain, for example, spinal stenosis, spondylolisthesis, and retrolisthesis.

Disc degeneration associated with the aging process is generally associated with the loss of proteoglycan from the nucleus pulposus of the spinal discs and a reduction of the disc's ability to absorb shock between vertebrae. Although some affected patients may not exhibit symptoms, many affected patients suffer from chronic back and/or leg pain. In some embodiments, the back pain can be caused by a degenerative disc disease or a herniated disc. Typically, when a patient has a herniated disc, the patient will exhibit severe or persistent radicular pain. When the herniated disc is in the lower back, persistent pain can originate in the back and often extends ("radiates") into the leg along the distribution of the sciatic nerve (lumbar radicular pain, or sciatica). In patients with herniated disc in the neck, the persistent pain can originate in the neck and often radiates into the arm. Patients can be diagnosed with herniated disc through a variety of characteristic findings. These include, for example: persistent radiating pain; characteristic findings on a physical exam indicative of nerve root irritation, injury or inflammation, such as limited mobility or range of motion due to pain; abnormalities in the strength and sensation of particular parts of the body that are found with a neurological examination, radiologic examination suggestive of a herniated disc. The better diagnostic imaging methods of the present application can assist the practitioner in confirming the location of the pain generator—in this case the herniated disc. Subsequently, a surgery can be performed and partial removal of the nucleus pulposus or annulus fibrosus can be performed. The better diagnostic imaging methods will guide the practitioner and he/she will now know that the right location is being operated on.

As used herein, a "degenerative disc disease" means any condition which results in degeneration of an intervertebral disc, including but not limited to, conditions caused by a disease, physical impact, mechanical wear, a pathogen, or an autoimmune response.

Degenerative disc disease can occur anywhere in the spine, such as the cervical spine (the neck), the thoracic spine (the part of the back behind the chest), the lumbar spine (lower back), and sacral spine (the part connected to the pelvis that does not move).

In some embodiments, the degenerative disc disease can include an intervertebral disc herniation. As used herein "intervertebral disc herniation" includes local displacement of disc material beyond the limits of the intervertebral disc space. The disc material may be nucleus pulposus, cartilage, fragmented apophysical bone, annular tissue or any combination thereof. Displacement of disc material may put pressure on the exiting spinal nerve and/or cause an inflammatory reaction leading to radiculopathy, weakness, numbness, and/or tingling in the arms or legs. Radiculopathy refers to any disease affecting the spinal nerve roots.

Intervertebral herniation can lead to conditions such as for example, sciatica, a compressed nerve, discogenic back pain, foraminal stenosis, pinched nerve, compressive neuropathy, chronic nerve pain, sensory and/or motor neuropathy, numbness or weakness, or the like. Thus, the better diagnostic imaging methods of the present application may be used to diagnose these diseases and/or conditions.

In some embodiments, intervertebral disc herniation includes a rupture of the annulus fibrosis, through which the inner disc material (nucleus pulposus) extrudes, protrudes, bulges, migrates and/or re-herniates. Sometimes disc extrusions may be displaced so much that it has lost continuity with the parent disc. When this happens the extrusion is called sequestration. Thus, the methods of the present application can be used to treat ruptures, protrusions, bulges, extrusions, re-herniation, and migration, fragmented, and/or sequestrated nucleus pulposus.

A "migrated disc or fragmented disc" refers to displacement of the disc material away from an opening in the annulus through which material has extruded. Sometimes migrated fragments will be sequestrated. For example, the nucleus pulposus may migrate away from the herniated disc so that there is sequestration in a different location in the spine that may lead to pinched nerve or spinal stenosis.

In general, most degenerative disc disease takes place in the lumbar area of the spine. Lumbar disc herniation occurs 15 times more often than cervical disc herniation, and it is one of the most common causes of lower back pain. The cervical discs are affected 8% of the time and the upper-to-mid-back (thoracic) discs only 1-2% of the time. Sometimes degenerative disc disease can lead to compression of the nerve roots of the spine resulting in very painful neurological symptoms. Nerve roots (large nerves that branch out from the spinal cord) may become compressed resulting in neurological symptoms, such as sensory or motor changes. For example herniation of the nucleus pulposus often is accompanied by lower back pain that worsens in the sitting position and pain that radiates to the lower extremities. The radiating pain, for example, in sciatica is often described as dull, burning or sharp pain, accompanied by intermittent sharp electric shock sensation, numbness, and tingling, motor or sensory defects of the respective nerve root and/or reflex abnormalities.

Figure 2:
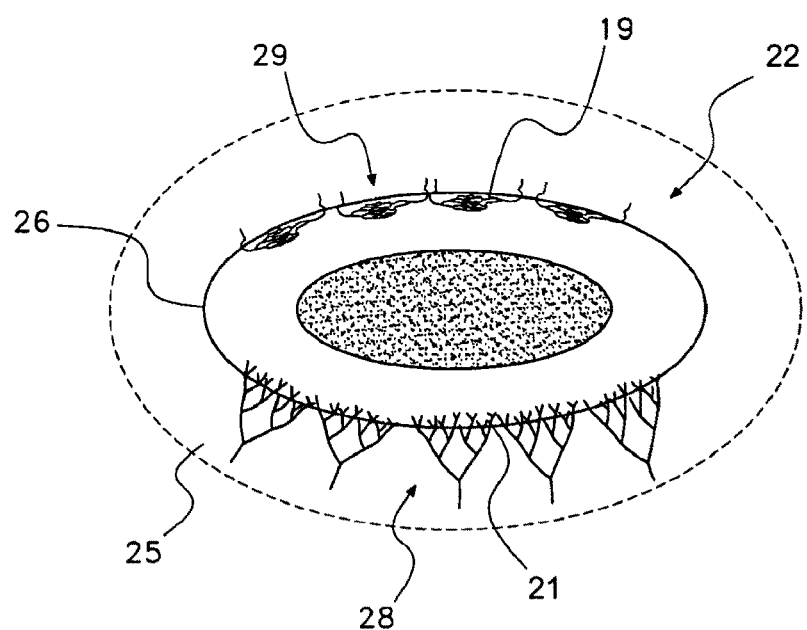
FIG. 2 illustrates a disc region that includes a disc having pain generators shown as centripetally invasive neuronal and vascular extensions in a degenerative disc.

For purposes of illustration only, referring to FIGS. 1 and 2, the spine is a remarkably strong and flexible structure that is capable of withstanding substantial forces. As shown in FIGS. 1 and 2, a spine 10 is formed from a plurality of vertebrae 12, each of which is individually separated from the other by a disc 20. The discs 20 abut the spinal cord, which runs through the spinal canal of the vertebrae 12. The discs 20 have several functions, one of which includes serving as shock absorbers for the vertebrae 12.

Each disc 20 is somewhat like a jelly donut, having a relatively tough outer layer called the annulus fibrosus that surrounds a gel-like inner layer called the nucleus pulposus. The annulus fibrosis is composed of concentric layers of intertwined annular bands, which are arranged to resist forces placed upon the spine 10. The cartilaginous endplate, adjacent to the disc 20, separates the nucleus pulposus and annulus fibrosus from the adjacent vertebrae 12. The posterior longitudinal ligament 30 strongly attaches to the annulus fibrosus. The nucleus pulposus is composed of cells from the primitive notochord, and contains significant amounts of substances capable of exciting, or increasing the excitability of, sensory nerves. These substances include prostaglandin E, histamine-like substances, potassium ions, lactic acid, and several polypeptide amines. These substances can be clearly imaged using the methods of the present application.

Pain arising from the disc 20 may be termed discogenic pain. Generally, though not always, to experience pain in a particular region the presence of nerve endings in that region is required. One source of pain is caused by the activation of specific nociceptors connected with C- and A-delta fibers. Another source of pain involves injury to sensory fibers, or damage to the central nervous system. Hence, the innervation of the disc 20 is of interest to the study of discogenic pain.

Branches 16 extend from the spinal cord, with sub-branches 18 innervating the disc 20. A meningeal branch 16 of the spinal cord, termed the recurrent sinuvertebral nerve, innervates the area around the disc 20. Exiting from the dorsal root ganglion and entering the foramen, the sinuvertebral nerve 16 divides into major ascending and lesser descending branches. The branches 18 generally innervate only the outer third of the annulus fibrosus, and hence typically do not enter into the inner two thirds of annulus fibrosus, nor into the nucleus pulposus, unless pathological conditions exist, such as for example, degenerative disc disease.

The discs 20 are surrounded by the interlacing nerve fibers 18. Although the nerve fibers 18, including the sinuvertebral nerve 16, are related to structures generally considered sympathetic, this does not necessarily mean that the nerve fibers 18 are fully sympathetic in function. Most such nerves 18 may have a sensory function. Moreover, the sympathetic nervous system is capable of interacting with sensory C-fibers, which are sensitizing nociceptors, thereby inducing further sympathetic activity in the spinal cord. Studies have demonstrated the presence of sensory fibers in the discs 20 of humans; substance P (SP) and calcitonin gene-related peptide (CGRP)-immunoreacitive (-IR) nerve fibers are also present in the disc 20. Because SP and CGRP are both expressed in nociceptive neurons and their axons, these SP- and CGRP-IR nerve fibers 18 within the disc 20 are thought to be involved in transmitting nociceptive information from the disc 20. Hence, the disc 20 itself can be a source of pain.

Normal discs 20 are rarely innervated deeper than the outer third of the annulus fibrosus. However, there are indications that degenerated or problematic discs 20 have nerve extensions that extend centripetally beyond the outer third of the annulus fibrosis, reaching as far as the inner third of the annulus fibrosis, or even into the nucleus pulposus. The invasion of such neuronal extensions may be a source of pain, particularly if they come into contact with those substances in the nucleus pulposus that are capable of exciting such neuronal extensions.

Back and neck pain can be caused by a degenerated disc. A degenerated disc may, but not necessarily always, show anatomical signs of degeneration, which can include changes in the height of the disc, the level of hydration of the disc, annular bulging, or the presence of tearing or osteophytes. A reduction in the height of the disc 20 may be one of the most common, early and easily detectable changes present in a degenerated disc. Another sign of degeneration is normally loss of the T2 weighted signal on an MRI scan; this is indicative of a loss of hydration of the nuclear tissue. The disc 20 may be any disc within a spinal column, including cervical, thoracic and lumbar discs.

Radiculopathy refers to disease of the spinal nerve roots (from the Latin radix for root). Radiculopathy produces pain, numbness, or weakness radiating from the spine. Radiculopathies are categorized according to which part of the spinal cord is affected. Thus, there are cervical (neck), thoracic (middle back), and lumbar (lower back) radiculopathies. Lumbar radiculopathy is also known a sciatica. Radiculopathies may be further categorized by what vertebrae they are associated with. For example, radiculopathy of the nerve roots at the level of the seventh cervical vertebra is termed C7 radiculopathy; at the level of the fifth cervical vertebra, C5 radiculopathy; at the level of the first thoracic vertebra, T1 radiculopathy; and so on.

Discs 20 are generally avascular, with the transport of nutrients and metabolites occurring primarily through diffusion. However, a degenerated disc 22, as shown in FIG. 2, tends to be more vascular than normal discs 20. This centripetally invasive vascularization 19 of the disc 22, also may have a similar neuronal invasion 21, with a perivascular nerve network with vasomotor or vasosensory functionalities. Further, increased vascularization of the disc 19 may be associated with increased innervation, and hence increased chances for discogenic pain.

Without wishing to be bound by theory, it is believed that invasion of the disc 25 by neuronal extensions 21 or vascular extensions 19 may be a source of discogenic pain. Thus, these vascular 19 or neuronal extensions 21 can be pain generators or give rise to pain generators. These invasive neuronal and vascular extensions can go as deep as in the middle of the central-nucleus region. As they get closer to the middle of the nucleus region that is when they have their highest predictive value as pain generators.

The current application provides better diagnostic imaging methods to diagnose degenerative disc disease by better imaging of these pain generators by providing a labeled diagnostic agent to the pain generator, such as for example, neuronal elements 28 and/or vascular elements 29 in a disc region 22. The disc region 22 includes the disc 25 that is believed to be a source of pain. Such disc 25 is typically a degenerated disc. The disc region 22 may extend as far as 5 cm from the outer surface of the annulus fibrosus 26 of the degenerative disc 25.

The diagnostic agent can be labeled, administered and then bind to the pain generator, where it can be imaged. Alternatively, the pain generator can produce chemical and/or biological marker in excess, which the diagnostic agent will bind to when a high concentration of the agent pools in that area, which can be clearly detected by the imaging techniques, such as for example, radiography, fluoroscopy, luminescence, PET, SPECT, CT, MRI, discography, myelogram, and/or X-ray imaging techniques.

Figure 3:
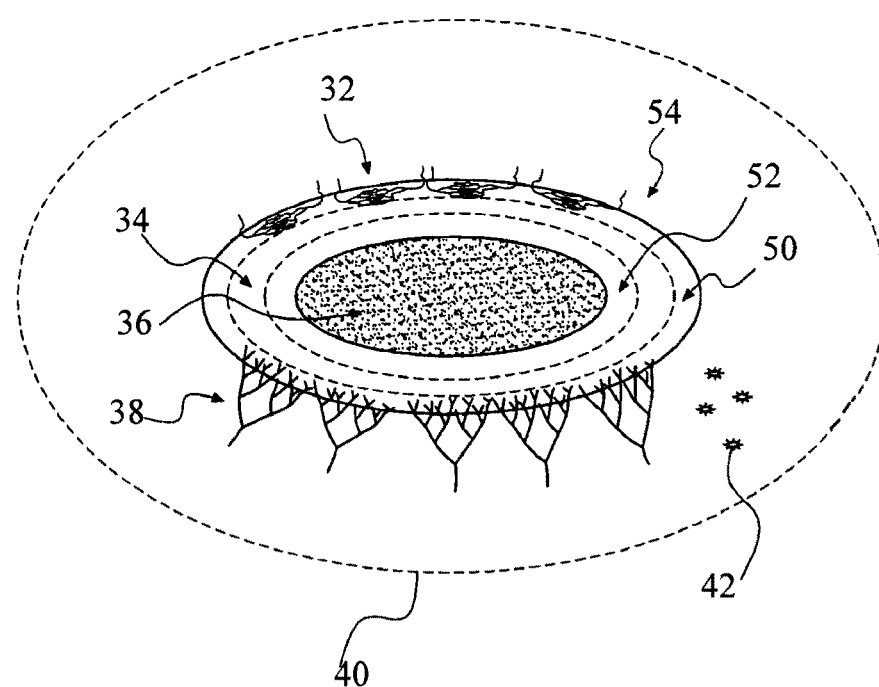

In alternative embodiments, as shown in FIG. 3, the diagnostic agent 42 may be delivered to the annulus fibrosus to image the pain generator shown as neuronal elements 38 and/or vascular elements 32 in a disc 40 causing the discogenic pain. As shown in FIG. 3, the diagnostic agent can be released by the annulus fibrosus, ideally immediately adjacent to, or within 5 cm of, the disc 40. Hence, the diagnostic agent may be disposed within the disc region 54 to target neuronal elements 38 and/or vascular elements 32. The diagnostic agent can bind the neuronal elements 38 and/or vascular elements 32 and upon imaging, they can be viewed and the pain generators identified. Alternatively, the diagnostic agent 42 can proceed into zones 52, 50 and 34 and proceed into the nucleus pulposus 36 and the agent can bind with any metabolic or inflammatory pain generators and then they can be viewed to determine if the amount of the labeled pain marker is outside of the normal range, which would indicate the location of the pain generator or suspected pain generator.

In some embodiments, the labeled pain marker can be administered intravenously, intramuscularly, subcutaneously or the like and the labeled pain marker can go through the general blood stream, where it will bind with the pain generator at or near the disc. Alternatively, the labeled pain marker can be administered locally directly into the disc, however, this may cause damage to the disc and eventually develop toward disc herniation and pain over the years.

Figure 4:
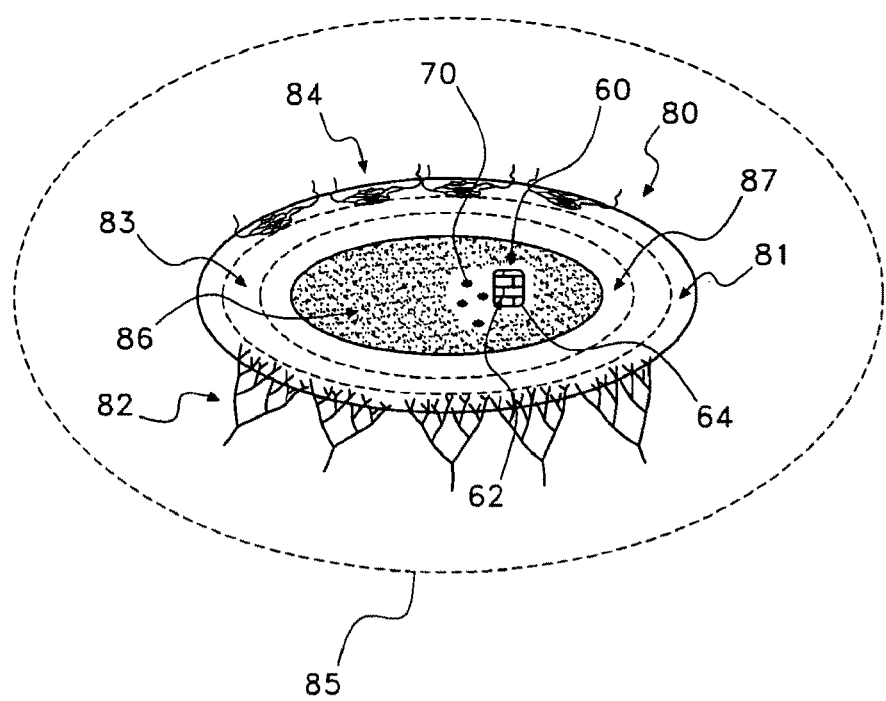
FIG. 4 illustrates an embodiment of the nucleus pulposus of a degenerative disc where the labeled agent is released and binds a pain marker near the neuronal and vascular extension, which will allow visualization of the neuronal and vascular extensions to locate the pain generators or suspected pain generators.

In alternative embodiments, as shown in FIG. 4, the diagnostic agent 70 may be delivered to the nucleus pulposus 86 to image the pain marker. In this embodiment, the diagnostic agent 70 can pass through zones 81, 83 and 87 of the disc and will bind with a pain marker 60, for example, an excessive amount of cytokine 62, which will generate a signal 64 from the excessive binding of a label and cause a "hot spot" when imaged. For example, the agent can bind with a cytokine and then the area can be viewed to determine if the amount of the labeled pain marker is outside of the normal range, which would indicate the location of the pain generator or suspected pain generator. This area can be diagnosed as the pain generator. In this way, the exact location of the pain generator can be determined.

The labeled pain marker or the labeled pain generator bound or free may be detected by imaging one or more of blood, cerebrospinal fluid, intercellular fluid, cellular or a tissue sample. The tissue sample can comprise neuronal, vascular tissue or any other appropriate bodily tissues that provide the selected pain-marker or pain generator that are associated with the specific pathological condition.

The labeled pain marker or the labeled pain generator measured or imaged are ideally associated with the pathological condition that is being diagnosed or treated. In one embodiment, for example, the pathological condition may be a degenerative disc disease, and the pain marker a labeled cytokine being measured may be released by the injured disc.

In some embodiments, the range of labeled pain marker or labeled pain generator detected can be 10%, 20%, 30%, 40%, 50%, 60%, 70%, 80%, 90%, 100%, or higher than the normal level of labeled pain marker or labeled pain generator present in the location in a healthy patient. Therefore, the image of the area(s) with the labeled pain marker or labeled pain generator will be visible on imaging and the pain generator or suspected pain generator can be diagnosed.

In the embodiment shown in FIG. 4, it will be understood that the labeled diagnostic agent can also target the pain generator directly (e.g., neuronal elements 82 and/or vascular elements 84) in the annulus fibrosis 80 that may cause the discogenic pain. As shown in FIG. 4, the diagnostic agent 70 can be released in nucleus pulposus 86, ideally immediately adjacent to, or within 5 cm of, the disc 85. Hence, the diagnostic agent may be disposed within the disc region 85 to target neuronal elements 82 and/or vascular elements 84, as well.

In some embodiments, the methods can be used to label an inflammatory, vascular, neuronal, and/or metabolic pain marker at a location inside of or adjacent to an intervertebral disc. This labeled pain marker, which will have affinity for the pain generator, will bind with the pain generator and, therefore, the pain generator will be labeled and then the area can be imaged and the pain generator, which is now labeled, diagnosed.

In some embodiments, the pain markers that can be labeled include labeling nerves, labeling nociceptors, labeling chemical factors that irritate nerves, labeling cells that produce chemical factors that irritate nerves; and labeling blood vessels that are typically in close approximation to nerves.

Neuronal Pain Markers

In the present application, the diagnostic agent can be used to label a neuronal pain marker, which after being labeled can bind to the pain generator. Alternatively, the diagnostic agent can be a labeled pain marker and then administered to the patient, where the labeled pain marker can bind to the pain generator and the pain generator can be imaged for its diagnosis.

The pain marker(s) are considered contributors in various ways to (or otherwise indicative of) the generation or transmission of discogenic pain. One such pain marker relates to the presence of nociceptors. Normally, intervertebral discs are substantially avascular and only sparsely innervated at the outer margins of the disc annulus. These unmyelinated, substance P (SP) or calcitonin gene-related peptide (CGRP) containing fibers are typically unresponsive and termed silent nociceptors. SP and CGRP are believed to be the sensory transmitters of nociceptive information. As degeneration proceeds, nerves can follow microvessels and grow deeper into discs, which may occur for example either peripherally or via the endplate. This nerve and vessel in-growth is facilitated by degeneration-related decreases in disc pressure and proteoglycan content. Thus by administering a diagnostic agent that binds SP or CGRP, the SP and CGRP conjugate will have an abnormally high concentration and, therefore, imaging will show a high signal to noise ratio (e.g., 2/1, 3/1, 4/1, 5/1, 6/1, 7/1, 8/1, 9/1, 10/1 etc.) and the pain generator will be clearly imaged and diagnosed in the area of "hot spots".

Diagnostic agents may be labeled in vivo by administering a label that binds with the pain marker. In some embodiments, the neuronal pain marker that can be labeled include, without limitation: TRK-α; anti-TRK α antibody; nerve growth factor (NGF); anti-NGF antibody; NGF antagonist; anti-NGF antagonist antibody; PGP 9.5; SYN; peripherin; or other form of nerve antibodies or related materials in general. Other materials such as neurofilament 200 kDa (NF200) may also be the target of such labeling and subsequent imaging.

In some embodiments, endogenous substances such as TrkA or NGF may be targeted as the pain markers for labeling, or related antibodies or other substances having particular binding affinity or specificity to such substances may be bound to them in the area of pain and then thereafter provide the binding site for targeted labels to be subsequently delivered. In this regard, it is to be appreciated that various forms of binding agents are broadly contemplated hereunder this description.

Nerves usually accompany blood vessels, but can be found as isolated nerves fibers in the disc matrix. These non-vessel-associated fibers found in back pain patients have been observed to express growth-associated protein 43 (GAP43) as well as SP. Small disc neurons contain CGRP and also express the high-affinity nerve growth factor (NGF) receptor, tyrosine kinase A (trkA). Disc inflammation has been observed to cause an increase in CGRP positive neurons. A recent study showed that NGF is expressed in microvascular blood vessels in a painful lumbar disc, and that there are trkA (TRK-α) expressing nerve fibers adjacent to the vessels that enter painful discs primarily through the endplate. Along with nerves growing into degenerated discs are specialized nerve support cells termed 'glia' or Schwann cells localized using glial fibrillary acidic protein (GFAP). Accordingly, various such materials may provide the requisite binding affinity or specificity to painful regions (or highly innervated regions) to play the role as the pain marker for the diagnostic agent to bind to or they may be labeled and then administered to identify the pain marker or the pain generator.

In one embodiment, for example, TrkA antibody (or other binding agent) is labeled and delivered for binding and visualization to the pain generator. In another embodiment, NGF itself is labeled and delivered as a diagnostic agent, which binds the pain marker TrkA.

In further embodiments, the resident quantities of these materials are treated as the pain markers themselves for targeted labeling, e.g. using antibodies or other agents with beneficial binding affinity and/or specificity to these types of resident compounds in painful regions. Some of these agents are further described in Published PCT Patent Applications are herein incorporated in their entirety by reference thereto: WO 2004/032870; WO 2004/058184; WO 2004/073653; WO 2004/096122; and WO 2005/000194.

The various compositions and methods described in these incorporated references may be adopted where appropriate to one of ordinary skill as a pain marker and/or pain marker target that when bound to the target can be used to identify the pain generator or suspected pain generator. For example without limitation, NGF antagonists, anti-NGF antibodies, anti-NGF antagonist antibodies, and various combinations or blends of these, or analog or derivatives thereof, may be labeled and delivered to their target and the pain generator determined. Moreover, additional compounds may also be included in the agent delivery scheme, or as additional targets for labeled markers, such as for example opioids, NSAID, or other molecules or drug agents related to pain therapy.

In some embodiments, the neuronal pain marker comprises a neuronal body, extensions of the neuron, such as axons, axonal branches, and dendrites, supporting cells, such as glial cells, astrocytes, Schwann cells, or microglia. These pain markers can have binding sites for the diagnostic agent to bind thereto and label the site for imaging so that the pain generator can be diagnosed.

In one embodiment, the neuronal pain marker may be a growth factor. Exemplary growth factors include nerve growth factor (NGF), brain-derived growth factor, glial-derived growth factor, neurotrophin-3, neurotrophin-4, insulin-growth factor, fibroblast growth factor and leukemia inhibitory factor. These neuronal pain markers can be labeled by delivery of a diagnostic agent to the site and then the area can be imaged. For example, labeled ReN-1820, which may also be a suitable active ingredient, is a recombinant protein that contains the binding domain of the NGF protein and acts as a soluble receptor to the endogenous NGF protein, thus when it binds to an active area of NGF at or near the disc, the area can be imaged and the pain generator identified. The ReN-1820 can also reduce the levels of NGF that can bind to NGF receptors found on neuronal elements, which may also reduce the pain and inflammation. ALE-0540, which may also be a suitable active ingredient, is an NGF receptor antagonist that can reduce pain and inflammation. See J. B. Owolabi et al., Characterization of antiallodynic actions of ALE-0540, a novel nerve growth factor receptor antagonist, in the rat, 289(3) J. PHARMACOL. EXP. THER. 1271-76 (1999). ALE-0540 can be labeled and administered to the patient. On imaging, the binding site can be viewed and the area where there is a high concentration can be the diagnosed as a pain generator.

In some embodiments, the label can be one or more multiple short-lived tracers that can be administered within a single session to assess various biological aspects of the tumor or the effects of an intervention which should also be applicable to discogenic pain diagnostic and treatment provided herein. For example, labeled pain markers or labeled diagnostic agents can be used to diagnose the pain generator such as neuronal elements including sensory, sympathetic neuronal extensions and glial supporting cells.

Neprilysin can be a labeled pain marker or labeled diagnostic agent that can detect a neuronal extension (a pain generator). Alternatively, a labeled diagnostic agent can be used that binds neprilysin and thus the pain generator can be identified. For example, associations have been observed between neprilysin expression and various types of cancer; and substance P sensory fibers are found in the degenerating disc. Therefore, neprilysin can be labeled to detect substance P, which on its binding can detect another pain marker (e.g., now labeled substance P) or a pain generator, such as a neuronal extension.

Neprilysin also known as membrane metallo-endopeptidase, neutral endopeptidase (NEP), CD10, and common acute lymphoblastic leukemia antigen (CALLA), is a zinc-dependent metalloprotease enzyme that degrades a number of small secreted peptides, most notably the amyloid beta peptide whose abnormal misfolding and aggregation in neural tissue has been implicated as a cause of Alzheimer's disease. Synthesized as a membrane-bound protein, the neprilysin ectodomain is released into the extracellular domain after it has been transported from the Golgi apparatus to the cell surface. In neurons, neprilysin is regulated by the protein nicastrin, a component of the gamma secretase complex that performs a necessary step in processing amyloid precursor protein to amyloid beta. Neprilysin is also associated with other biochemical processes, and is particularly highly expressed in kidney and lung tissues.

In some embodiments, a labeled pain marker or a labeled diagnostic agent can be administered that inhibits neprilysin's activity against signaling peptides such as enkephalins, substance P, endothelin, and atrial natriuretic factor. This can also result in analgesia and when the labeled pain marker or the labeled diagnostic agent is administered, and binds these signaling peptides, the pain generator can be identified.

In one embodiment, the labeled pain marker or labeled diagnostic agent can comprise octreotide, which targets somatostatin receptors (SSTRs) expressed on breast cancer cells and can also bind to sensory A and B fibers (e.g., pain generators) that can be found in the degenerating disc.

Targeted magnetic resonance contrast agents have enabled the imaging of biological processes in vivo, and current insights have opened up new perspectives for the monitoring and diagnosis of many diseases. In the past, octreotide has been used with a contrast agent for targeting somatostatin receptors (SSTRs) expressed on breast cancer cells, and to evaluate the detection capabilities of a molecular probe using magnetic resonance (MR) imaging in an in vivo mouse model of breast carcinoma. Octreotide (OCT) was conjugated with polyethylene glycol-coated ultrasmall superparamagnetic iron oxide (USPIO) nanoparticles by an ethyl-3-(dimethylaminopropyl) carbodiimide (EDC)-mediated reaction. This compound can be used to detect the pain generator or suspected pain generator in back or neck pain.

In one embodiment, the labeled pain marker or labeled diagnostic agent can comprise hydroxyephedrine. Hydroxyephedrine is a noradrenaline analog that can label the sympathetic system and neuroblastoma of sympathetic origin—sympathetic neurons controlling blood vessel activity is also found in the degenerating disc. Thus, labeled hydroxyephedrine can be used to detect the pain marker or pain generator. The $^{11}$C-labeled tracer meta-hydroxyephedrine ($^{11}$C-HED) is also a noradrenaline analog that was developed to visualize the sympathetic nervous system with PET. Initial clinical studies show a rapid uptake of $^{11}$C-HED in localized tumors of this system. Therefore, this compound can be used to detect the pain generator or suspected pain generator in degenerative disc disease.

In one embodiment, the labeled pain marker or labeled diagnostic agent comprises iobenguane, also known as metaiodobenzylguanidine or mIBG, which is a radiopharmaceutical neuroblastoma of sympathetic origin. This compound can be used to detect sympathetic neurons controlling blood vessel activity found in the degenerating disc.

In some embodiments, the pain generator or suspected pain generator can be associated with glial cells. Glial cells use angiogenesis and metabolic pain markers and therefore, these cells can be used to identify the pain generator.

In some embodiments, the labeled pain marker or diagnostic agent can be used to detect vascular extensions and based on angiogenesis detection a labeled anti-angiogenesis agent can be administered to identify the pain generator. Some examples of labels that can detect angiogenesis and their half-life are listed in Table A below:

TABLE A

| Imaging | Isotope | Half-life (hours) |
| --- | --- | --- |
| γ-emitter (SPECT) | 99mTc | 6 |
| | 111In | 67 |
| | 123I | 13 |
| | 125I | 59 days |
| B+-emitter (PET) | 18F | 2 |
| | 11C | 20 min |
| | 64Cu | 13 |
| | 68Ga | 1 |
| | 124I | 100 |

In some embodiments, the labeled pain marker or diagnostic agent can detect hypoxia, which triggers angiogenesis. In some embodiments, the labeled pain marker or diagnostic agent can detect a protein variant or antibody that can bind to VEGF protein or receptor. An example of such antibody is bevacizumab.

In some embodiments, the labeled pain marker or labeled diagnostic agent can be an inhibitor of vascular endothelial growth factor (VEGF) receptors, FMS-like tyrosine kinase 3 (FLT3), c-KIT, and platelet-derived growth factor (PDGF), which will allow antiangiogenic properties. For example, sunitinib malate is a potent inhibitor of VEGF receptors, FLT3, c-KIT, and PDGF. Also, sorafenib inhibits VEGF receptors, PDGF receptors, FLT3, RAF-1, and BRAF. Therefore, sunitinib malate or sorafenib can be labeled and used to detect the pain marker and/or pain generator.

In some embodiments, the labeled pain generator or labeled diagnostic agent can be one or more chemicals, peptides, proteins and/or antibodies which bind to the αvβ3 integrin receptor, VEGF and its receptor, prostate-specific membrane antigen (PMSA), matrix metalloproteinases (MMPs) and Robo-4. Positron Emission Tomography (PET) and Single Photon Emission Computed Tomography (SPECT) can be used with radiotracer-based imaging modalities for noninvasive depiction and quantification of biochemical processes to diagnose the pain generator.

In some embodiments, the labeled pain marker or diagnostic agent can target the αvβ3 integrin receptor. The αvβ3 integrin is a transmembrane protein containing two non-covalently bound subunits, α and β. Integrin αvβ3 is minimally expressed on normal quiescent endothelial cells, but significantly upregulated on activated endothelial cells during angiogenesis. In addition, αvβ3 is expressed on the cell membrane of various tumor cell types such as: ovarian cancer, neuroblastoma, breast cancer, melanoma, among others. αvβ3 integrin interacts with the arginine-glycine-aspartic acid (RGD) amino acid sequence present in extracellular matrix proteins such as vitronectin, fibrinogen, and laminin. Therefore, labeled RGD-containing peptides (e.g., radiolabeled cyclic RGD peptides) can target with gamma- or positron-emitting radionuclides αvβ3 expressed cells, which can allow the practitioner to identify the pain marker or pain generator. For example, 18F-labeled galactosylated cyclic pentapeptide ([18F]Galacto-RGD) or [18F]-AH111585 or [18F]FDG, have a high affinity and selectivity for αvβ3. These agents can be used to identify the pain generator or pain marker. 99mTc-labeled RGD-containing peptide (NC100692) is used in ischemic models and showed high uptake in areas of neovascularization with αvβ3 integrin overexpression. In these models it was shown that NC100692 bonded to αvβ3-expressing endothelial cells in the regions of angiogenesis. Therefore, these labeled RGD peptides can be used to detect the pain marker or pain generator.

In some embodiments, the labeled pain marker or diagnostic agent can comprise a multimeric RGD peptide. These include cyclic RGD multimers including E[c(RGDfK)]2-based dimers and E[c(RGDyK)]2-based dimers labeled with 64Cu or 18F for PET imaging. Other RGD dimers, tetramers, and even octamers labeled with different radionuclides can target integrin αvβ3. In addition, incorporation of the right spacer between the RGD motifs can enhance the affinity for αvβ3 and improve the uptake by the pain generator even further. Among mono-, di-, tetra- and octameric cyclo (RGDfK)-based peptides, the octamer can have the highest αvβ3 affinity and usually the highest uptake.

In some embodiments, the labeled pain marker or diagnostic agent can target VEGF receptors. VEGF is a key regulator of angiogenesis. The expression of VEGF is upregulated by environmental stress caused by hypoxia, anemia, myocardial ischemia and tumor progression to initiate neovascularization. VEGF binds two related receptor tyrosine kinases (RTKs), VEGFR-1 and VEGFR-2. Both receptors contain seven Ig-like domains in the extracellular domain, a single transmembrane region and a consensus tyrosine kinase sequence that is interrupted by a kinase-insert domain. VEGFR-1 binds VEGF with a higher affinity compared to VEGFR-2 (Kd:25 vs. 75-250 pM).

In some embodiments, the labeled pain marker or diagnostic agent binds to VEGF. For example, the labeled diagnostic agent can be bevacizumab. Bevacizumab is a humanized variant of the anti-VEGF-A monoclonal antibody (mAb) Radiolabeled bevacizumab can be used in non-invasive VEGF imaging to detect a pain marker or pain generator. The radiolabeled bevacizumab that can be used is 89Zr-bevacizumab or 111In-bevacizumab as a specific VEGF tracer. In some embodiments, the labeled diagnostic agent comprises labeled VEGF121 with 64Cu via DOTA for PET imaging of VEGFR expression.

Inflammatory/Metabolic Pain Markers

In the present application, the diagnostic agent can be used to label an inflammatory pain marker or metabolic pain marker, which after being labeled can bind to the pain generator or accumulate in the pain generator. Alternatively, the diagnostic agent can be a labeled pain marker and then administered to the patient, where the labeled pain marker can bind to or accumulate in the pain generator and the pain generator can be imaged for its diagnosis.

In one embodiment, the pain marker can be an inflammatory or proinflammatory marker. For example, a neuronal pain generator is generally embodied by the need for the intradiscal nociceptors to be sensitized, and thus generally involves agents providing such sensitization. This can occur for example via cytokines, which are typically small, secreted proteins that mediate and regulate inflammation. They generally act over short distances, short times, and at very low concentrations. Cytokines typically function by binding to specific membrane receptors, which often then signal the cell via second messengers to alter gene expression. Responses to cytokines include increasing or decreasing expression of membrane proteins (including cytokine receptors), cell proliferation, and secretion of effector molecules. Cytokines may act on the cells that secrete them (autocrine action), on nearby cells (paracrine action), or in some instances on distance cells (endocrine action). It is common for different cells types to secrete the same cytokine or for a single cytokine to act on several different cell types (pleiotropy).

Cytokines are redundant in their activity, and are often produced in a cascade, as one cytokine stimulates its target cells to make additional cytokines. Cytokines can also act synergistically or antagonistically. Elevated levels of certain cytokines have been measured in human discs, and are associated with degeneration and pain. Such major cytokines have been observed to include interleukin-1, -6, and -8, tissue necrosis factor-alpha (TNF-α), macrophage migration inhibitory factor (MIF), and prostaglandin E2 (PGE2). Thus one can administer one or more labeled diagnostic agents that bind to inflammatory pain markers, such as for example, interleukin-1, -6, and -8, tissue necrosis factor-alpha (TNF-α), macrophage migration inhibitory factor (MIF), prostaglandin E2 (PGE2) and allow one to image these pain markers. When concentrations of these bound labeled cytokines are abnormally high, a "hot spot" will appear in the image and the user will know the location of the pain generator or suspected pain generator. Alternatively, one can administer one or more labeled pain markers, such as for example, interleukin-1, -6, and -8, tissue necrosis factor-alpha (TNF-α), macrophage migration inhibitory factor (MIF), prostaglandin E2 (PGE2) and allow them to bind to the pain generator. On imaging, the pain generator will now be localized to a particular area and the pain generator can be diagnosed.

The source of cytokines can be circulating inflammatory cells, such as for example in the case of herniated discs, or disc cells, such as for example in the case of contained disc degeneration. These pro-inflammatory stimuli can trigger cells to initiate a number of catabolic programs meant to stimulate tissue repair and remodeling that includes production of matrix metalloproteinases 1, 9 and 13. During this wound healing process, cytokines are also often involved in stimulating angiogenesis and granulation tissue formation.

In one particular embodiment, cytokines and/or their cell-surface receptors are imaged at sites of inflammation in vivo using labeled markers, such as radiolabels. In particular beneficial examples, cytokines are labeled with one or more of the following, without limitation: iodine-123, iodine-125, iodine-131, technetium-99m, fluorine-18, or indium-111. In addition, positron-emitting radioisotopes (for example and without limitation fluorine-18) can be imaged using positron emission tomography (PET) or positron emission tomography-computed tomography (PET-CT). Example of fluorine-18 compounds that can be imaged by PET or other imaging techniques include, for example, comprises [18F] FDG (2'-deoxy-2'-fluro-D-glucose) or [18F] 1-(3-fluoropropyl)-4-(4-cyanophenoxymethyl) piperidine or [18F] AH-111585. Other radiolabeled compounds can be imaged for example using single photon emission computerized tomography (SPECT).

It is also to be appreciated that MRI may be employed according to further embodiments for visualizing or observing accumulation or binding of various labeled markers described herein, such as for example in applying gadolinium as a marker tagged to or conjugated with certain labels to be bound to a pain marker. Moreover, nanoparticles such as gold or iron oxide may be used as labels or markers to bind and thereafter be viewed or selectively targeted for therapy using appropriate visualization or treatment modalities, respectively.

According to still further embodiments contemplated hereunder, inflammatory markers themselves may be labeled and delivered to targeted tissues and imaged to identify the location of the pain generator or suspected pain generator. Exemplary cytokines, as discussed above, include, without limitation, TNF-α, MIF, PGE2 or certain interleukins such as IL-1, 6, or 8 (or other interleukins).

Other markers considered indicative of certain activities or environmental considerations believed linked to pain, and thus appropriate targets for labeling as pain markers, include: pH (e.g. in particular marking low pH as indicator of pain; or $O_2$ levels, e.g. in particular marking low $O_2$ as indicator of pain).

Two pain markers of interest are IL-1b and TNF-α. IL-1b and TNF-α have been observed to demonstrate overlapping pro-inflammatory effects, activate common signaling cascades, and induce similar target genes. Effector cascades mediating inflammatory responses to IL-1 and TNF-α include the mitogen-activated protein kinases (MAPK), NF-κβ, and prostaglandin signal transduction pathways. The signaling molecule nitric oxide may also form an important component of the inflammatory cascade. These markers can be labeled and administered to detect the pain generator or suspected generator or alternatively they can act as the target for the labeled diagnostic to bind thereto.

In some embodiments, imaging via labeling tissue necrosis factor-alpha (TNF-α) can provide one particular beneficial example of marking for imaging a pro-inflammatory cytokine that can chemically hypersensitize the intervertebral disc and spinal nerve roots, thereby contributing to low back pain. It is believed that levels of TNF-α are increased after compression-induced degeneration of the intervertebral disc. Therefore, TNF-α antibodies can be labeled with I-125 and administered intravenously so that variations in TNF-α content can be imaged in vivo. Increased uptake will be seen on imaging in areas of the injured disc and thus the pain generator can be identified.

TNF-α antibodies are available from Johnson & Johnson as Remicade® (infliximab) that can be labeled and be used as the diagnostic agent. This example illustrates using a therapeutic compound that actually provides some pain-related therapy (e.g. TNF-α antibodies or other form of blocker) that is also used to image the location of the pain being treated.

In some embodiments, it is to be appreciated that targeted agents, such as antibodies as herein described by way of example, may provide the label for imaging, or may take the form of the targeted factor (either by itself or by virtue of its conjugation or binding with a first resident factor). In the later case, delivery of the first factor is then subjected to subsequent labeling by delivery of a second agent as the labeled marker (again either by its imagability itself or as bound, associated, or conjugated with the first delivered agent to the region imaged).

In some embodiments, cells that produce or are associated with inflammatory markers can also be labeled with targeted markers and thereafter imaged as an indicator that pain exists in the area. For example, disc cells that are actively synthesizing inflammatory factors may be labeled as such (or components thereof may be labeled). Inflammatory cells that are attracted to painful discs, such as for example leukocytes, may be labeled and imaged for this purpose.

The present application can be used to label a metabolic pain marker, such as those in the MAPK pathway, which can be imaged and the pain generator located. For example, MAPKs form an intracellular signaling pathway built upon a self-propagating phosphorylation system. Activation of MAPKs are one of the pivotal intracellular pathways triggered by cytokine receptors. Three MAPK subgroups have been identified: extracellular signal regulated kinase (ERK); the Jun $NH_2$-terminal kinases (JNK); and p38. In chondrocytes, ERK activation occurs in response to diverse stimuli, while JNK and p38 is only seen in response to IL-1 and TNF-α. This signaling pathway is thought responsible for cartilage degradation. JNK and p38 are collectively termed stress activated protein kinases (SAPKs). The signal is initiated by membrane-proximal small GTPases of the Rho family, activation of MLK, and phosphorylation and activation of MKK3/6 that in turn phosphorylates and activates p38.

One endpoint of MAPK activation is the production of the phosphorylated active activator protein 1 (AP-1) transcription factor (heterodimer of c-Jun and c-Fos), which in turn, can influence chondrocyte collagenase activity. AP-1 plays a central role in the transcriptional regulation of many MMP genes including collagenase and stromelysin. Similarly, MIF activates the MAPK pathway and AP-1 leading to cell proliferation, and $PGE_2$ production, which eventually promotes monocyte/macrophage activation. Certain published data suggests that MIF is in particular upregulated under conditions of chronic emotional stress and can potentiate elevated levels of other inflammatory factors such as for example those examples herein described. Accordingly, labeling MIF provides yet a further embodiment of the various present aspects. JNK and p38 are essential for IL-1 induction of mmp-13, while ERK pathway is not. p38 is essential for multiple inflammatory genes, including Il-1, TNF-α, Il-6, stromelysin-1 (mmp-3) and mmp-1.

It will be appreciated by those skilled in the art that various metabolic markers associated with pathways or molecular cascades associated with pain may provide the target for the labeled diagnostic and subsequent imaging as herein described, and various such markers are provided here as beneficial examples which, though of particular value, are also not intended to limit broad aspects contemplated hereunder. In addition, such otherwise indigenous materials may also demonstrate selective uptake in tissues associated with pain. In such case, these otherwise indigenous materials (or synthetic or other biologic constructs similar to them, such as analogs or derivatives thereof) may also be harnessed and labeled for delivery as the labeled marker. Moreover, due to their selective uptake, particular accumulated concentrations of certain molecules in areas of pain also render them viable targets as the pain markers themselves for labeling and identification of the pain generator.

In addition to the MAPK induction, IL-1 and TNF-α activate NF-κβ. NF-κβ is a transcription factor that exists in a latent form in the cytoplasm of unstimulated cells and is composed of a transcriptionally active dimer (p65 and p50) bound to an inhibitor protein (Iκβ). NF-κβ is activated by a large number of different signals that include similar cell stress signals that activate SAPKs. IL-1 and TNF-α trigger the phosphorylation and degradation of Iκβ resulting in the release of NF-κβ to enter the nucleus. NF-κβ activation occurs through a cascade starting with NF-κβ-inducing kinase (NIK), which then phosphorylates and activates the inhibitor of NF-κβ. Iκβ kinases. Phosphorylation of Iκβ results in ubiquitination and degradation of Iκβ inhibitory subunit, allowing NF-κβ to translocate to the nucleus where it acts as a transcription factor and regulates its target genes, which include collagenase MMP-1; and COX-2. These metabolic pain markers can be labeled and administered to detect the pain generator or suspected generator or alternatively they can act as the target for the labeled diagnostic to bind thereto.

In one embodiment, the methods can be used to label a metabolic pain marker, such as in the prostaglandin pathway, which can be imaged and the pain generator located. Eicosanoids are signaling molecules that act in an autocrine fashion in the prostaglandin pathway. Pro-inflammatory stimuli can lead to increased phospholipid-derived eicosanoid synthesis that involves a cascade of three enzyme reactions. First, arachidonic acid (AA) is liberated from its phospholipid storage sites by phospholipase A2 (PLA2). The next rate-limiting step is conversion of AA to prostaglandin H2 by cyclooxygenase (COX). The prostaglandin pathway is stimulated by IL-1b. This cytokine increases the activity of PLA2 and induces COX-2 gene expression by binding to a specific cell-surface receptor (IL-1 RI) that ultimately leads to increases in COX-2 promoter activity via the NF-κβ pathway. In chondrocytes, COX activity is not increased by TNF-α. Rather, TNF-α can amplify COX activity in IL-1 stimulated cells. Prostaglandin $E_2$ ($PGE_2$) stimulates the catabolism of chondrocytes, having both anti-proliferative and pro-apoptotic effects. An increase in $PGE_2$ may therefore tip the balance toward catabolism. These pain markers can be labeled and administered to detect the pain generator or suspected generator or alternatively they can act as the target for the labeled diagnostic to bind thereto.

In one embodiment, the methods can be used to label a metabolic pain marker, such as nitric oxide, which can be imaged and the pain generator located. Nitric oxide (NO) is a small signaling molecule that is part of the catabolic program in chondrocytes induced by IL-1 and TNF-α. It is produced within the cell by the inducible isoform of NO synthase (iNOS), and then passes readily through the cell membrane to affect neighboring cells. Because it has a short half-life (5 to 10 seconds) it acts only locally, yet it plays an important role in the pathophysiology of arthritic disease. It has been shown to: induce apoptosis (by stimulating release of cytochrome c from mitochondria) and inflammation (by activating COX and PLA2; suppress collagen and proteoglycan synthesis; and upregulate MMP synthesis. IL-1 and TNF-α increase the gene expression and synthesis of iNOS, through the transcription factors NF-κβ and AP-1. Activation of NF-κβ is an essential step for iNOS induction. Also, there is some evidence that the MAPK p38 may be involved in the activation of NF-κβ and subsequent iNOS expression, since p38 is reported to be required for IL-1-induced iNOS expression in chondrocytes.

In some embodiments, the labeled diagnostic agent comprises [18F] FDG (2'-deoxy-2'-fluro-D-glucose) or [18F] 1-(3-fluoropropyl)-4-(4-cyanophenoxymethyl) piperidine or [18F] AH-111585 and these can be taken up by the pain generator and the area imaged via PET techniques to locate the pain generator.

In one embodiment, the metabolic pain marker comprises a labeled sugar, such as for example, 18F-fluorodeoxyglucose, which in the past, has been used to detect glioma using imaging techniques. This compound can be used to diagnose a pain generator.

In one embodiment, the metabolic pain marker comprises a labeled amino acid, such as for example, methionine (MET), tyrosine, leucine and amino acid derivatives such as 18F-fluorethyltyrosine, in the past have been used to detect glioma using imaging techniques. These compounds can be used to diagnose a pain generator.

In one embodiment, the inflammatory pain marker is from a DNA salvage pathway. The DNA salvage pathway acts as a recycling mechanism that helps with DNA replication and repair. All cells use this biochemical pathway to different degrees. But in lymphocytes and macrophages, the cells of the immune system that initiate immune response, the pathway is activated at very high levels. A labeled pain marker, such as for example, [18F]-2-fluoro-D-(arabinofuranosyl)cytosine ([18F]-FAC) can detect deoxycytidine salvage process and presence/activity of macrophages and T cells, an hallmark of chronic inflammation. This can be used to diagnose the pain generator.

In one embodiment, the inflammatory pain marker is a labeled inflammatory marker comprising a radiotracer (11) C-(R)-PK11195, which allows the in vivo imaging by positron emission tomography (PET) in humans of the translocator protein 18 kDa (TSPO), also called peripheral benzodiazepine receptor (PBR), which is a marker of inflammation or can be a pain generator.

Vascular Pain Markers

The present application can be used to label a vascular pain marker, which can be imaged and the pain generator located. Alternatively, a labeled diagnostic agent can be administered and bind the pain marker to create a labeled pain marker, which can then bind with a pain generator. The binding is specific and can be ionic, non-covalent or covalent bonding. Examples of non-covalent binding include, affinity, ionic, van der Waals (e.g., dipole/dipole or London forces), hydrogen bonding (e.g., such as, for example, between polynucleotide duplexes), or hydrophobic. Where association is non-covalent, the association between the entities can be specific. Non-limiting examples of specific non-covalent associations include the binding interaction between the binding of a substrate to its enzyme; the binding of a ligand to a receptor specific for the ligand; the binding of an antigen to an antibody to an antigen against which the antibody is raised or the like. In some embodiments, specific binding includes, for example, between two entities, may include a binding affinity of at least $10^6$, $10^7$, $10^8$, $10^9$ $M^{-1}$, or $10^{10}$ $M^{-1}$.

For example, some blood vessels typically run along side and co-existent with nerves, pain markers related to blood vessels may also be labeled by administering the diagnostic agent that specifically binds with the blood vessels and imaged as indicia regarding vascularity itself, or as a measure of concomitant innervation in an area. Such constitutes a further embodiment contemplated hereunder, and described in some further detail as follows. For example, PECAM (platelet endothelial cell adhesion molecule) and/or CD34 may be appropriate targets to be marked by the diagnostic agent as they are related to blood vessels and thus indicating their presence in a particular location or region could be used to identify the pain generator. Another example of an appropriate pain marker includes GFAP (Glial fibrillary acidic protein) for endothelial cells. Other microvessel-related factors are considered. In some embodiments, the vascular element includes blood vessels, capillaries and/or endothelial cells.

In some embodiments, the vascular pain marker can be any marker involved in angiogenesis. In general, angiogenesis is the process by which new blood vessels are formed from pre-existing capillaries or post capillary venules. Angiogenesis is also involved in degenerative disc disease. In many instances, the process begins with the activation of existing vascular endothelial cells in response to a variety of cytokines and growth factors. To date, numerous angiogenic factors have been identified, including the particularly potent factor VEGF (vascular endothelial growth factor). VEGF was initially purified from the conditioned media of folliculostellate cells and from a variety of cell lines. More recently a number of structural homologs and alternatively spliced forms of VEGF have been identified. The various forms of VEGF bind as high affinity ligands to a suite of VEGF receptors (VEGFRs). VEGFRs are tyrosine kinase receptors, many of which are important regulators of angiogenesis. The VEGFR family includes 3 major subtypes: VEGFR-1, VEGFR-2 (also known as Kinase Insert Domain Receptor, "KDR", in humans), and VEGFR-3. Among VEGF forms, VEGF-A, VEGF-C and VEGF-D are known to bind and activate VEGFR-2.

VEGF, acting through its cognate receptors, can function as an endothelial specific mitogen during angiogenesis. In addition, there is substantial evidence that VEGF and VEGFRs are up-regulated in conditions characterized by inappropriate angiogenesis, such as cancer. As a result, a great deal of research has focused on the identification of therapeutics that target and inhibit VEGF or VEGFR. Therefore, VEGF and its subtypes can be pain markers that the diagnostic agent targets.

In some embodiments, the following agents can be labeled and bind the pain marker and/or pain generator and then it can be imaged. Some examples of such agents include, without limitation, labeled adalimumab, Infliximab, Etanercept, Pegsunercept (PEG sTNF-R1), Onercept, Kineret® (anakinra), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, AMG 108, or capsaiein, civanide, TNFRc, ISIS2302 and GI 129471, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL6 mAb (MRA, Tocilizumab, Chugai), HMGB-1 mAb (Critical Therapeutics Inc.), anti-IL2R antibody (daclizumab, basilicimab), ABX (anti IL-8 antibody), recombinant human IL-10, HuMax IL-15(anti-IL 15 antibody) or combinations thereof.

Different modes of imaging are contemplated in the present application, as apparent to one of ordinary skill to match the labeled pain marker to the pain generator. A variety of diagnostic imaging procedures may be used to acquire information related to the targeted pain marker and/or pain generator and related spatial location relative to surrounding tissues. This information may be processed and converted into a representation that may be displayed or otherwise conveyed to a practitioner in a manner sufficient and useful to understand the spatial location of the associated pain and/or pain generator.

Accordingly, different types of sensors, data acquisition systems, processors, and displays may be used in different combinations to convert the labeled marker to useful information to such practitioners. Many of these are commercially available in sufficient form to readily integrate with the diagnostic agent, pain marker and the pain generator and delivery systems herein described (which may further include therapeutic agents) in an overall system sufficient to provide useful information in medical patient management. Such diagnostic imaging procedures include, for example, radiography, fluoroscopy, luminescence, PET, SPECT, CT, MRI, and/or X-ray imaging techniques.

Administration

In various embodiments, the diagnostic agent may be parenterally administered. The term "parenteral" as used herein refers to modes of administration, which bypass the gastrointestinal tract, and include for example, injectable, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof.

The diagnostic agent, in various embodiments, may be formulated for parenteral administration (e.g. by injection, for example bolus injection or continuous infusion), subcutaneous injection, or intramuscular injection and may be presented in unit dose form in ampoules, pre-filled syringes, small volume infusion or in multi-dose containers with an added preservative. The diagnostic agent may take such forms as suspensions, solutions, or emulsions in oily or aqueous vehicles, and may contain formulatory agents such as suspending, stabilizing an/or dispersing agents. Alternatively, the diagnostic agent may be in powder form, obtained by aseptic isolation of sterile solid or by lyophilisation from solution, for constitution with a suitable vehicle, e.g. sterile, pyrogen-free water, NS, D5W, etc. before use.

Parenteral administration may additionally include, for example, an infusion pump that administers a diagnostic agent composition through a catheter near the spine or one or more inflamed joints, an implantable mini-pump that can be inserted at or near the target site, an implantable controlled release device or sustained release delivery system that can release a certain amount of the composition per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and reservoir. The third contains an inert gas, which provides the pressure needed to force the diagnostic agent composition into the peristaltic pump. To fill the pump, the diagnostic agent composition is injected through the reservoir fill port to the expandable reservoir. The inert gas creates pressure on the reservoir, and the pressure forces the diagnostic agent composition through a filter and into the pump chamber. The diagnostic agent composition is then pumped out of the device from the pump chamber and into the catheter, which will direct it for deposit at the target site. The rate of delivery of diagnostic agent composition is controlled by a microprocessor. This allows the pump to be used to deliver similar or different amounts of diagnostic agent composition continuously, at specific times, or at set intervals between deliveries.

Potential diagnostic agent composition devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering diagnostic agent composition to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. In various embodiments, a method for delivering a diagnostic agent composition at or near the target tissue site of a patient is provided. The method comprising inserting a cannula at or near a target tissue site and administering the diagnostic agent composition at the target site beneath the skin of the patient.

In some embodiments, it is preferred that the diagnostic agent is not administered locally into the spine to prevent damage to any of the discs.

In some embodiments, the practitioner will look for irritation, injury, inflammation, limited mobility or range of motion due to pain, abnormalities in the strength and sensation of particular parts of the body, further neurologic and radiologic examinations (e.g., MRI, CT, CT myelography, etc.) to explain the persistent pain symptoms the patient experiences. Such pain can exhibit as, for example, radiating pain, weakness, or numbness in the legs, back, arms, or neck. This will allow the practitioner to identify additional suspected pain generators. Subsequent neurologic and radiologic examinations can be performed, if needed, to determine the location of the pain generators (e.g., pain generators in nerve areas, facet joints, medial branch nerves, sacroiliac joints, discs) and rule out selective areas where the pain generator is not located. A surgical procedure can now be scheduled to provide long-term relief at the site of the pain generator. In this way, operating on the wrong area and/or suspected pain generator is avoided.

In some embodiment, the diagnostic agent can comprise a matrix to keep the diagnostic agent at a target tissue site so as to allow better imaging. Examples of suitable matrixes that can be a carrier for the diagnostic agent include, without limitation, poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, poly(glycolide-,-caprolactone), ϵ-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), Matrigel®, or combinations thereof. In one embodiment, the matrix is Matrigel®, which comprises a gelatinous protein mixture secreted by Engelbreth-Holm-Swarm (EHS) mouse sarcoma cells and is available from by BD Biosciences. These matrixes will delay release of the diagnostic agent for better imaging.

In some embodiments, the matrix comprises at least 10 wt %, at least 50 wt. %, at least 60 wt. %, at least 70 wt. %, at least 80 wt. %, at least 85 wt. %, at least 90 wt. %, at least 95 wt. %, or at least 98% or at least 99 wt. % of the formulation.

In some embodiments, the diagnostic agent is in the matrix in an amount that comprises at least 0.1% wt %, at least 0.5 wt. %, at least 1 wt. %, at least 5 wt. %, at least 10 wt. %, at least 15 wt. %, at least 20 wt. %, at least 25 wt. %, or at least 30% or at least 35 wt. % or at least 40 wt. % or at least 45 wt. % of the formulation.

The diagnostic agent can be in the matrix in different forms including, for example, capsules, microspheres, microparticles, microcapsules, microfibers particles, nanospheres, nanoparticles, coating, matrices, wafers, pills, pellets, emulsions, liposomes, micelles, gels, or other delivery formulation or a combination thereof.

Having now generally described the invention, the same may be more readily understood through the following reference to the following examples, which are provided by way of illustration and are not intended to limit the present invention unless specified.

EXAMPLES

Introduction

The disc is considered the largest avascular structure in the human body and this particularity plays a major role in the progressive degeneration of the aging disc. For unknown reasons the nucleus of the disc loses much of its vital blood supply during the first decade of life. Without sufficient nutrients the cells of the disc begin to die, the water content of the nuclear pulposus decreases and the annulus fibrosus becomes disorganized. These matrix and morphologic changes are common to the general degenerative process of the spine and are often not associated with pain in humans as well as in animal models. For example, the "sand rat" has been studied for the spontaneous occurrence of disc degeneration into the lower section of its spine which becomes more prominent with aging (Gruber et al., 2002:2005). In this naturally occurring model of disc degeneration, signs of disc degeneration included morphological changes as well as changes in the composition of the disc tissue. However, it does not appear that these morphological changes were associated with pain. Similarly, in the stab injury model, mechanical rupture of the disc in rats and rabbits is associated with changes in the matrix components, functional impairment and pain are observed soon after injury and resolve after a few weeks (Masuda et al., 2005: Rousseau et al, 2007; Zhang et al., 2009).

Stab injury of the ovine model (Melrose et al., 2002) also induces changes in the matrix components that appeared as soon as 3 months after injury but contrary to the rat and rabbit models, lasted for up to 26 months after injury. In addition in the ovine model, blood vessel ingrowths from the periphery of the disc to the deeper layers of the disc were observed as soon as 3 months, peaked at about 12 months with progressive reduction observed at 26 months post-injury. Actively growing neuronal extensions from the periphery to the deeper layers of the disc were observed at a later timepoint (i.e. 6 months) and remained prominent at 26 months post-injury. There are no validated pain measures for large animals and pain signals were not reported.

Increased density of neuronal extensions have been observed in painful discs from human patients (extracted at time of surgery) from the vertebral endplate to the inner portion of the annulus fibrosus (Brown et al, 1997; Freemont et al., 1997; Palmgren et al., 1996; Coppes et al., 1997; Peng et al., 2005). The prevalence of an abnormal innervation of the annulus fibrosus was 3-5 times higher in painful discs than in asymptomatic aging discs and the presence of neuronal extensions within the nucleus pulposus was found only in painful discs. These neuronal extensions derived from sympathetic and nociceptive fibers which control vessel function and sensory signals, respectively.

It was discovered that induction of growth of neuronal or vascular extensions can change the recovery pattern following disc injury and trigger progressive increase in pain signals toward the development of a chronic pain condition. In this experiment, NGF or nerve growth factor was used, which is one of the most common and potent endogenous molecule that promote growth of neuronal cells. It was also shown to have neuroprotective properties in various neuronal injury models. VEGF or vascular growth factor was also used, which is one of the most common and potent endogenous molecule that promotes growth of blood vessels. CFA or complete Freund's adjuvant was also used, which is a well known pro-inflammatory molecule that has chemotactic properties and can attract immune cells.

Consistent with previous reports, mechanical rupture of the disc in rats was associated with pain symptoms that were observed soon after injury and resolve after a few weeks in the control group. However, discal injection of NGF or VEGF following disc injury was associated with a completely different pattern of recovery. Pain signals were 2 times lower soon after injury relative to the control group which is associated with the tissue repair function of NGF and VEGF. However, the long term effect of NGF and VEGF is growth of neuronal and vascular extensions which were associated with progressive increase of pain signals that were up to 2 times higher in the growth factor groups relative to control groups at 3 weeks post-injury. Discal injection of the pro-inflammatory factor CFA was associated with pain signal similar to the control group soon after injury but that were sustained over time which is also a sign of chronic pain development.

Accumulation of immune cells as well as increased in pro-inflammatory molecules and neuronal and vascular growth factors are often associated with tissue injury and participate in tissue repair and resolution of pain signals. However, sustained levels of these repair factors may also trigger the development of chronic pain conditions. Local accumulation of highly metabolically active cells as well as angiogenesis (i.e. growth of vascular extensions) are also common cancer features that have been studied for both therapy and diagnostic purposes. Similarly, abnormal growth of neuronal extensions can be responsible for certain types of brain tumors and have been extensively studied.

In this example, it is proposed to use the imaging markers developed for the diagnostic of tumors to the field of back pain as it relates to the visualization of accumulation of active immune cells, presence of pro-inflammatory molecules and abnormal growth of vascular and neuronal extensions. Alone or in combination with the current diagnostic tools, this new imaging test will help localize the specific pain generator(s) in individuals suffering from low back pain and insure appropriate treatment. Because this diagnostic can evaluate the progression of the disease (i.e. a condition getting worse as the signal is increasing or reaching deeper layers of the disc), it will also enable the development of new treatments for the different stages of the disease and enable the physician to objectively follow the effect of the therapies prescribed.

Example 1

Optimization of the Surgical Techniques and Formulation that Allow for Delivery and Retention of a Growth Factor within the Disc Trying to inject a solution into the disc was very challenging due to the size of the rat disc which is not bigger than about 2 mm3. During those studies we used a solution of a dextran-color dye with a MW of 10,000 Da which is similar to the MW of NGF to be able to assess the retention of the injected solution into the disc over a few days. During preliminary studies developed were surgical techniques that allowed for precise detection of the L4-L5 disc and intra-discal injection with minimal disturbance of the tissue surrounding the disc. During those early studies, the injection method including the creation of a space in the disc by blowing air with the needle that allows for the injection of a 10 ul volume of solution into the disc was optimized. From these early preliminary studies, it was very clear that the dye-solution was coming out of the disc as soon as it was injected into the disc. Two general strategies were evaluated to fix this problem: (1)—Plug the hole left by the needle after intra-discal injection and (2)—Use a solution that solidifies into the disc after injection (1)—Plugging the hole left by the needle after intra-discal injection: All sorts of glue-like or fibrous materials were tested to plug the hole left by the needle after injection including a gel foam pad and gel foam gel currently used in clinic to plug small holes in membranes, as well as glue, resin and silicone. None of these approaches succeeded in keeping the dye solution in the disc for 24 hours. Poking the needle through the gel foam pad and then through the disc was also not effective.

(2)—Use a solution that solidifies into the disc after injection: The dye was diluted in a solution of Matrigel which is used as a matrix to cover the bottom of Petri ditch and provide attachment and growth factor support to neurons cultured in vitro. This approach seemed to retain some of the dye in the disc after injection, mostly within the needle track and was used in further development.

Figure 5:
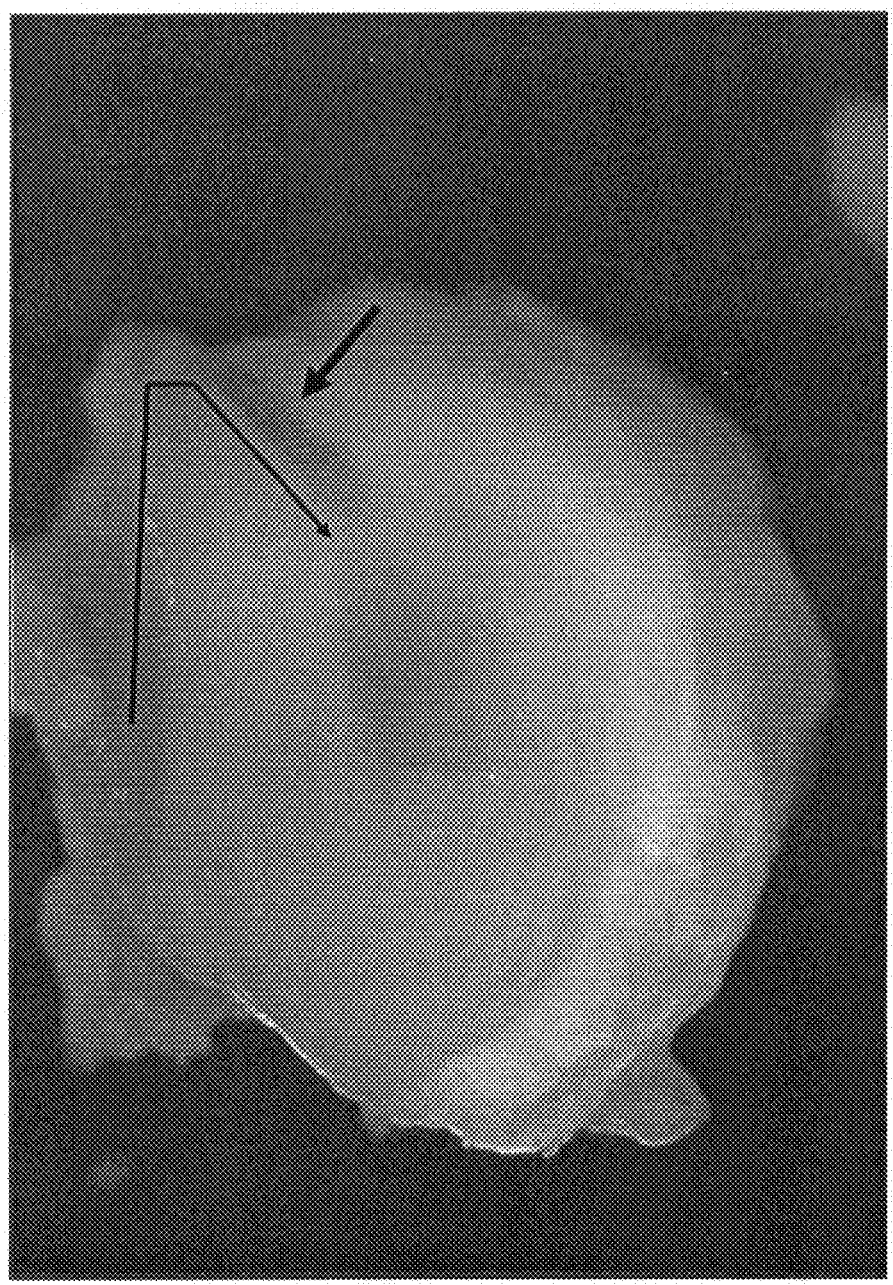
FIG. 5 illustrates a dye containing a growth factor placed into a nucleus pulposus of an intervertebral disc.

Surgical techniques were developed including puncture of the disc and removal of the nucleus pulposus to allow for the deposition of our growth factors. To improve retention in the disc, the growth factors were mixed in Matrigel which is an injectable solution that forms a gel at body temperature. Using these techniques I was able to reproducibly show retention of a dye within the disc up to 72 hours post-injection. A picture of the disc is shown in FIG. 5. The dye was found within the needle track line (short thick arrow) in most cases which, even if not optimal, could be sufficient to create a path for growth of neuronal and/or vascular extensions from outside the disc where they are normally found toward the inner layers of the disc (long thin arrow).

Example 2

Measure of Discogenic Pain Following Disc Injury and Discal Injection of Factors that Induce Inflammation or Growth of Neuronal or Vascular Extension Numerous pain testing scales have been developed in rats to evaluate analgesic strategies in animals before attempting clinical trials. Mechanical allodynia is the evaluation of the response of a rat to a stimulus that is normally not painful and does not induce a pain response. Investigators use Von Frey fibers of increasing diameters applied to the paw of the rat to evaluate its mechanical allodynia threshold. A modified version of this test, called "at-level" allodynia has been developed to measure abnormal pain that develops above and below the site of spinal cord lesion in rat spinal cord injury model (Gris et al., 2004). In this modified version, a Von Frey fiber of a fix diameter (2 g) is applied 10 times above and below the site of injury and the number of pain response is recorded. This method was applied to measure the allodynic response around the area of the injured disc which is indicative of discogenic pain. For this study, different growth factors were dissolved in the Matrigel and were injected in the L4-L5 rat disc using the delivery method developed during the previous experiment (Step 1 presented above). Three different growth factors were evaluated: (1) 10 ug of a rat nerve growth factor or NGF-β (Sigma), that can directly induce the growth of neuronal pain fibers, (2) 10 ug of a vascular endothelial growth factor or VEGF because it can promote the growth of vascular extension that may be required before neurons can growth into the disc (Sigma), (3) 10 ul of a pro-inflammatory factor or Complete Freund's Adjuvant or CFA (Each mL contains 1 mg of *Mycobacterium tuberculosis* (H37Ra, ATCC 25177), heat killed and dried, 0.85 mL paraffin oil and 0.15 mL mannide monooleate Sigma.) Mechanical "at-level" allodynia was evaluated over a 3-week period following intra-discal injection.

Figure 6:
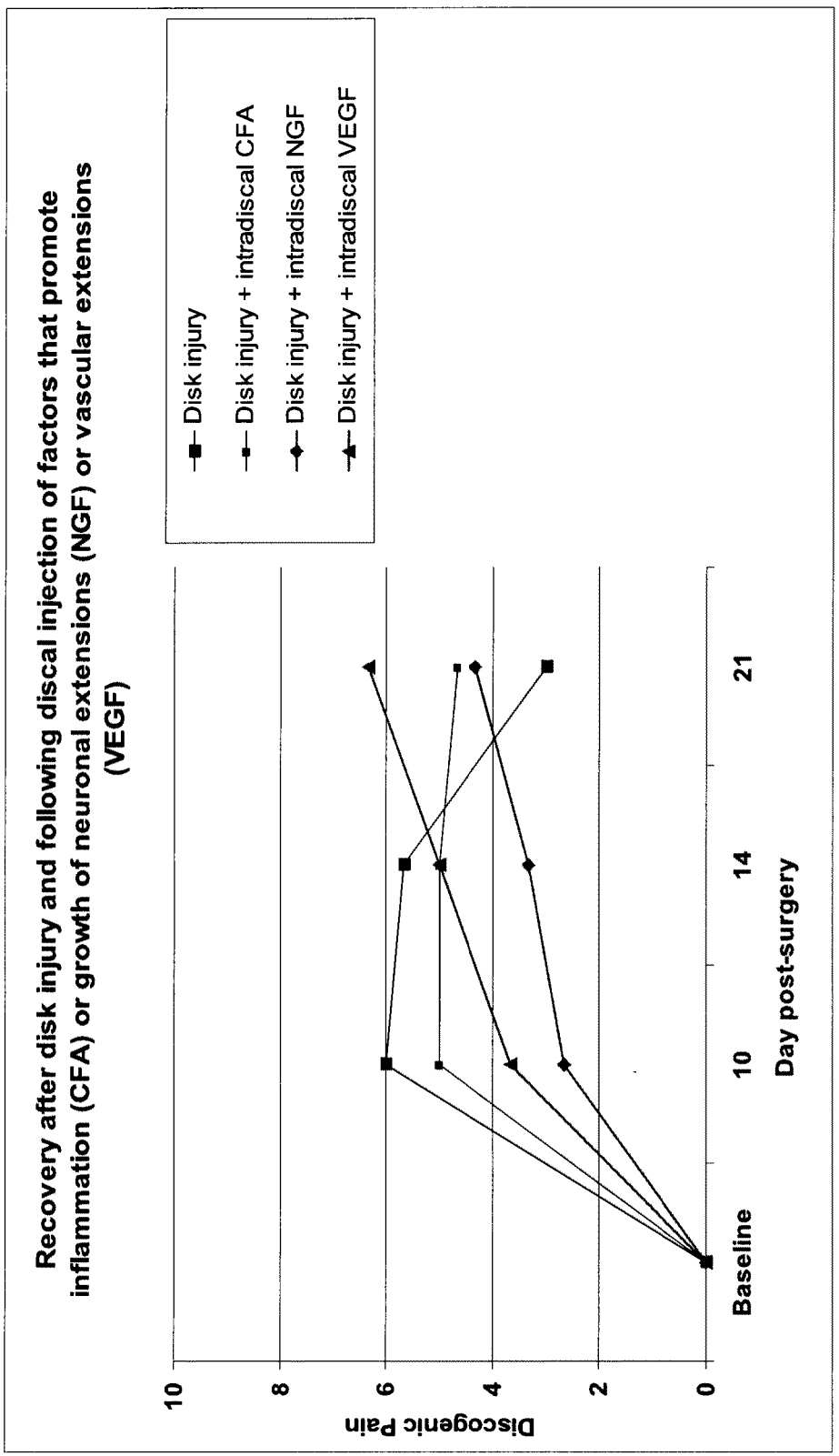
FIG. 6 is a graphic illustration of discogenic pain testing following injection of saline or of a neuronal growth factor (NGF) or a vascular growth factor (VEGF) or a pro-inflammatory factor (CFA) into intervertebral discs of rats.

Following injection of saline or of a neuronal growth factor (NGF) or a vascular growth factor (VEGF) or a pro-inflammatory factor (CFA) into one disc, rats were evaluated using a discogenic pain test over 3 weeks post-injury. FIG. 6 illustrates the results.

As previously reported, transient symptomatic pain that was reduced by half 3 weeks after injury to the disc was observed. Discal injection of NGF or VEGF was associated with a completely different pattern of recovery. Pain signals were 2 times lower soon after injury relative to the control group (disc injury) which is associated with the tissue repair function of NGF and VEGF. However, the long term effect of NGF and VEGF is growth of neuronal and vascular extensions, which were associated with progressive increase of pain signals that were up to 2 times higher in the growth factor groups relative to control groups at 3 weeks post-injury. Discal injection of the pro-inflammatory factor CFA was associated with pain signals similar to the control group soon after injury but that were sustained over time which is also a sign of chronic pain development.

These results demonstrate that NGF and VEGF can be used as pain markers, and when labeled, allow imaging of the pain marker and detection of pain generators or suspected pain generators. These results also indicates that induction of growth of neuronal and vessel extensions is associated progressive increase in discogenic pain and that labeling of those extensions can reveal pain marker and detection of pain generators or suspected pain generators. Finally, these results indicate that induction CFA-derived inflammation which includes recruitment and activation of inflammatory and immune cells to the site of injection (here the disc) is associated with development of discogenic pain and that recruitment and activation of inflammatory and immune cells to the site of injection can reveal pain marker and detection of pain generators or suspected pain generators.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method for diagnosing a pain generator or a suspected pain generator in a patient suffering from neck or back pain, the method comprising administering a diagnostic agent comprising a tracer that specifically binds to a pain marker at a location inside of or adjacent to an intervertebral disc in the patient suffering from neck or back pain thereby labeling the pain marker with the diagnostic agent; allowing the labeled pain marker to bind the pain generator or suspected pain generator; and comparing the amount of labeled pain marker in a location inside of or adjacent to the intervertebral disc to a normal range of the labeled pain marker inside of or adjacent to an intervertebral disc via imaging, wherein the amount of the labeled pain marker outside of the normal range indicates the location of and diagnoses the pain generator or suspected pain generator, and the labeled pain marker bound to the pain generator or suspected pain generator can be 30% or higher than the normal range of labeled pain marker or labeled pain generator present, wherein the tracer has a binding affinity of at least $10^8 M^{-1}$, and the pain marker comprises vascular endothelial growth factor, and the diagnostic agent is disposed in a matrix to retain the diagnostic agent at the location inside of or adjacent to the intervertebral disc in the patient, the diagnostic agent being in an amount of at least 35 wt. % of the matrix in microfiber particle form.

2. A method according to claim 1, wherein the imaging is a radiography, fluoroscopy, luminescence, PET, SPECT, CT and/or MRI imaging procedure.

3. A method according to claim 1, wherein the matrix comprises a polymer comprising polyethylene glycol-poly (lactide-co-glycolide) (PEG-PLG).

4. A method for diagnosing a pain generator or a suspected pain generator in a patient suffering from neck or back pain, the method comprising administering a diagnostic agent comprising a tracer that specifically binds to a pain marker at a location inside of or adjacent to an intervertebral disc in the patient suffering from neck or back pain thereby labeling the pain marker with the diagnostic agent; allowing the labeled pain marker to specifically bind to the pain generator or suspected pain generator; and comparing the amount of labeled pain marker in a location inside of or adjacent to an intervertebral disc to a normal range of the labeled pain marker inside of or adjacent to an intervertebral disc via imaging, wherein the amount of the labeled pain marker outside of the normal range indicates the location of the pain generator or suspected pain generator and the labeled pain marker bound to the pain generator or suspected pain generator can be 30% or higher than the normal range of labeled pain marker or labeled pain generator present, wherein the tracer has a binding affinity of at least $10^8 M^{-1}$, and the pain marker comprises vascular endothelial growth factor, and the diagnostic agent is disposed in a matrix to retain the diagnostic agent at the location inside of or adjacent to the intervertebral disc in the patient, the diagnostic agent being in an amount of at least 35 wt. % of the matrix in microfiber particle form, and the diagnostic agent is administered by intravenous, intramuscular, intrathecal, subcutaneous, epidural, intra-discal, peridiscal, peridural, perispinal administration or a combination thereof.

5. A method according to claim 4, wherein the imaging is performed using radiography, fluoroscopy, luminescence, PET, SPECT, CT and/or MRI imaging techniques.

6. A method for diagnosing a pain generator or a suspected pain generator in a patient suffering from degenerative disc disease, the method comprising administering a diagnostic agent comprising a labeled pain marker that is labeled with a tracer that specifically binds to the pain marker in a location inside of or adjacent to an intervertebral disc in the patient suffering from degenerative disc disease; and comparing the amount of the labeled pain marker in a location inside of or adjacent to an intervertebral disc to a normal range of the labeled pain marker inside of or adjacent to an intervertebral disc via imaging, wherein the amount of the labeled pain marker outside of the normal range indicates the location of the pain generator or suspected pain generator and the labeled pain marker bound to the pain generator or suspected pain generator can be 30% or higher than the normal range of labeled pain marker or labeled pain generator present, wherein the tracer has a binding affinity of at least $10^8 M^{-1}$, and the pain marker comprises vascular endothelial growth factor, and the diagnostic agent is disposed in a matrix to retain the diagnostic agent at the location inside of or adjacent to the intervertebral disc in the patient, the diagnostic agent being in an amount of at least 35 wt. % of the matrix in microfiber particle form.

7. A method according to claim 6, wherein a plurality of labeled pain markers are determined at a plurality of sites that triangulate the pain generator or suspected pain generator.

8. A method according to claim 6, wherein the imaging is performed using radiography, fluoroscopy, luminescence, PET, SPECT, CT and/or MRI imaging techniques.

* * * * *